(12) United States Patent
Pascal et al.

(10) Patent No.: US 10,653,311 B1
(45) Date of Patent: May 19, 2020

(54) HOME OCT WITH AUTOMATIC FOCUS ADJUSTMENT

(71) Applicant: Notal Vision Ltd., Tel Aviv (IL)

(72) Inventors: Amit Pascal, Haifa (IL); Gidon Goren-Gratzyani, Givatayim (IL)

(73) Assignee: NOTAL VISION LTD., Tel-Aviv (IL)

( * ) Notice: Subject to any disclaimer, the term of this patent is extended or adjusted under 35 U.S.C. 154(b) by 0 days.

(21) Appl. No.: 16/439,587

(22) Filed: Jun. 12, 2019

(51) Int. Cl.
  *A61B 3/10* (2006.01)
  *A61B 3/00* (2006.01)
  *A61B 5/00* (2006.01)
  *A61B 3/15* (2006.01)

(52) U.S. Cl.
  CPC ............ *A61B 3/102* (2013.01); *A61B 3/0025* (2013.01); *A61B 3/0075* (2013.01); *A61B 3/152* (2013.01); *A61B 5/004* (2013.01); *A61B 5/0066* (2013.01)

(58) Field of Classification Search
  CPC ..... A61B 3/102; A61B 3/0025; A61B 3/0075; A61B 3/152; A61B 5/004; A61B 5/0066
  USPC ........................................ 351/200, 205, 206
  See application file for complete search history.

(56) References Cited

U.S. PATENT DOCUMENTS

| | | | |
|---|---|---|---|
| 5,094,521 A | 3/1992 | Jolson et al. | |
| 5,838,424 A | 11/1998 | Wawro et al. | |
| 6,149,275 A | 11/2000 | O'Shea | |
| 6,980,363 B1 | 12/2005 | Takagi et al. | |
| 7,270,413 B2 | 9/2007 | Hirohara et al. | |
| 8,348,429 B2 | 1/2013 | Walsh et al. | |
| 8,384,908 B2 | 2/2013 | Sugita et al. | |
| 8,398,236 B2 | 3/2013 | Juhasz et al. | |
| 8,500,725 B2 | 8/2013 | Raksi | |
| 8,534,837 B2 | 9/2013 | Sayeram et al. | |
| 8,668,336 B2 | 3/2014 | Buckland et al. | |
| 8,842,287 B2 | 9/2014 | Yazdanfar et al. | |
| 9,144,379 B1 | 9/2015 | Sims | |
| 9,186,057 B2 | 11/2015 | Borycki et al. | |
| 9,192,295 B1 | 11/2015 | Hathaway et al. | |
| 9,420,947 B2 | 8/2016 | Wei et al. | |
| 9,538,916 B2 | 1/2017 | Muto | |

(Continued)

FOREIGN PATENT DOCUMENTS

WO 2016004385 1/2016

OTHER PUBLICATIONS

"U.S. Appl. No. 16/404,311," filed May 6, 2019.
(Continued)

*Primary Examiner* — Tuyen Tra
(74) *Attorney, Agent, or Firm* — Kilpatrick Townsend & Stockton LLP

(57) ABSTRACT

An optical coherence tomography (OCT) system for imaging a retina applies a user specific focus correction to focus a sample arm light beam on the user's retina. An OCT image detector generates an OCT signal. A control unit monitors the OCT signal, controls a reference arm optical path length adjustment mechanism to identify a length of the reference arm optical path for which the OCT signal corresponds to an OCT image of the retina, and varies an operational parameter of the sample arm light beam focus mechanism over a range, while maintaining the length of the reference arm optical path for which the OCT signal corresponds to the OCT image of the retina, to identify a focus correction for the user, based on the OCT signal, for application to the sample arm light beam.

21 Claims, 17 Drawing Sheets

(56) References Cited

U.S. PATENT DOCUMENTS

| | | |
|---|---|---|
| 2003/0063386 A1 | 4/2003 | Slawson et al. |
| 2008/0259274 A1 | 10/2008 | Chinnock |
| 2009/0180074 A1 | 7/2009 | Benyamini et al. |
| 2009/0268020 A1 | 10/2009 | Buckland et al. |
| 2013/0033593 A1 | 2/2013 | Chinnock et al. |
| 2013/0162948 A1 | 6/2013 | Yazdanfar et al. |
| 2013/0235344 A1* | 9/2013 | Buckland ............... A61B 3/102 351/206 |
| 2014/0002792 A1 | 1/2014 | Filar |
| 2014/0009741 A1 | 1/2014 | Levien et al. |
| 2014/0125952 A1 | 5/2014 | Buckland et al. |
| 2014/0132924 A1 | 5/2014 | Sagano et al. |
| 2014/0240674 A1 | 8/2014 | Wei et al. |
| 2014/0340642 A1 | 11/2014 | You et al. |
| 2015/0292860 A1* | 10/2015 | Podoleanu ......... G01B 9/02004 356/456 |
| 2015/0294147 A1 | 10/2015 | Wisweh |
| 2015/0305618 A1 | 10/2015 | Buckland et al. |
| 2015/0313467 A1 | 11/2015 | Sakai et al. |
| 2016/0026847 A1 | 1/2016 | Vugdelija et al. |
| 2016/0135681 A1 | 5/2016 | Wakil et al. |
| 2016/0143529 A1 | 5/2016 | Miyashita et al. |
| 2016/0183788 A1 | 6/2016 | Abramoff et al. |
| 2017/0042422 A1 | 2/2017 | Sakai et al. |
| 2017/0071466 A1 | 3/2017 | Kowal et al. |
| 2017/0172407 A1 | 6/2017 | Kowal et al. |
| 2017/0215725 A1 | 8/2017 | Ishiai |
| 2017/0224208 A1 | 8/2017 | Bublitz et al. |
| 2017/0227350 A1* | 8/2017 | Sarunic ............... G01B 9/02004 |
| 2017/0251920 A1 | 9/2017 | Tokuda et al. |
| 2019/0090735 A1 | 3/2019 | Fujii et al. |
| 2019/0254514 A1 | 8/2019 | Westphal et al. |

OTHER PUBLICATIONS

"U.S. Appl. No. 16/424,246," filed May 28, 2019.
"U.S. Appl. No. 16/439,587," filed Jun. 12, 2019.
Chakravarthy et al., "Automated Identification of Lesion Activity in Neovascular Age-Related Macular Degeneration", Opthalmology, vol. 123, No. 8, Aug. 2016, pp. 1731-1736.
PCT/IL2018/051172, "International Search Report and Written Opinion", dated Feb. 27, 2019, 12 pages.
PCT/IL2018/051174, "International Search Report and Written Opinion", dated Feb. 26, 2019, 8 pages.
U.S. Appl. No. 16/404,311, "First Action Interview Pilot Program Pre-Interview Communication", dated Aug. 15, 2019, 4 pages.
U.S. Appl. No. 16/424,246, "First Action Interview Pilot Program Pre-Interview Communication", dated Jul. 31, 2019, 4 pages.
U.S. Appl. No. 16/425,362, "First Action Interview Pilot Program Pre-Interview Communication", dated Aug. 27, 2019, 4 pages.
U.S. Appl. No. 16/425,362, "Non-Final Office Action", dated Aug. 23, 2019, 13 pages.
U.S. Appl. No. 16/404,311, Final Office Action dated Feb. 28, 2020, 17 pages.

* cited by examiner

FIG. 5a

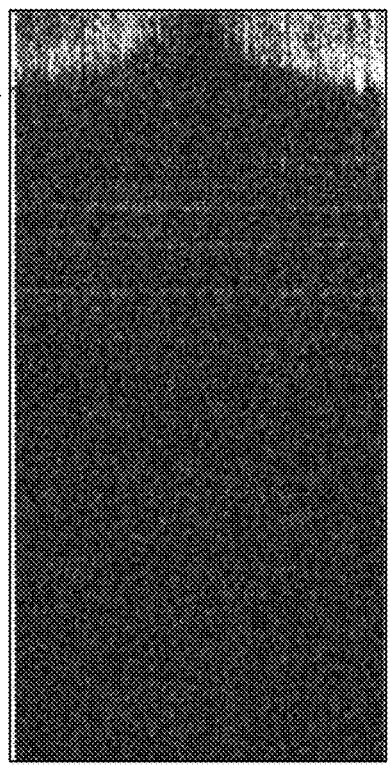

No "cross correlation" signal

This is an auto correlation signal from the retina that during the signal search should be ignored - 128

| Time AU | Reference arm position AU |
|---|---|
| 0 | 100 |

FIG. 5b

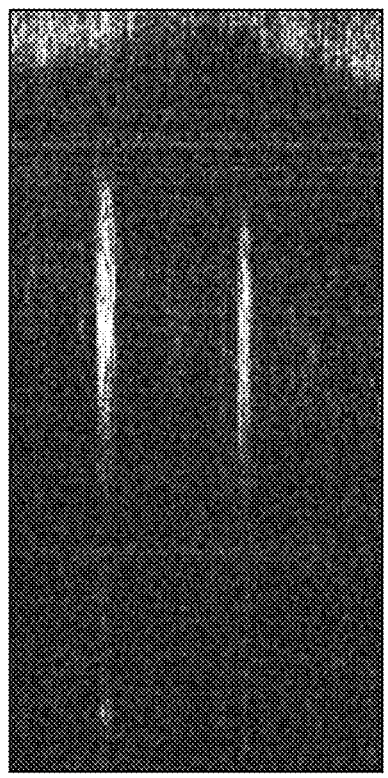

Example of a cross correlation signal- Ghost, while reference mirror moving

This is a cross correlation signal from the retina, during the signal search, this is an ghost/artifact that should be ignored - 132

| Time AU | Reference arm position AU |
|---|---|
| 1 | 90 |

FIG. 5c

Example of a cross correlation signal- Ghost, while reference mirror moving

| Time AU | Reference arm position AU |
|---|---|
| 2 | 80 |

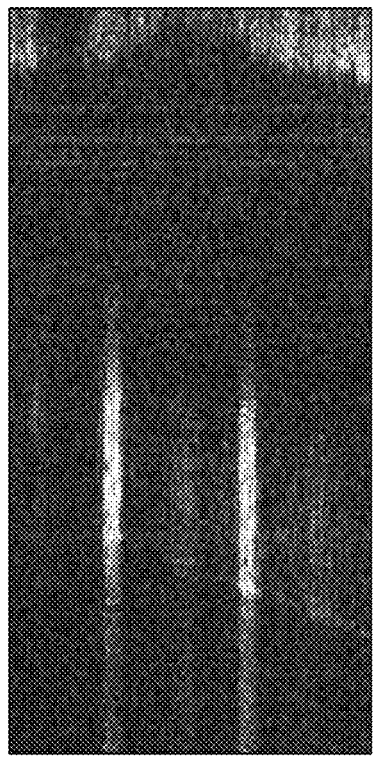

This is a cross correlation signal from the retina, during the signal search - this is an ghost/artifact that should be ignored - 136

Example of a cross correlation signal- Ghost, while reference mirror moving

| Time AU | Reference arm position AU |
|---|---|
| 3 | 70 |

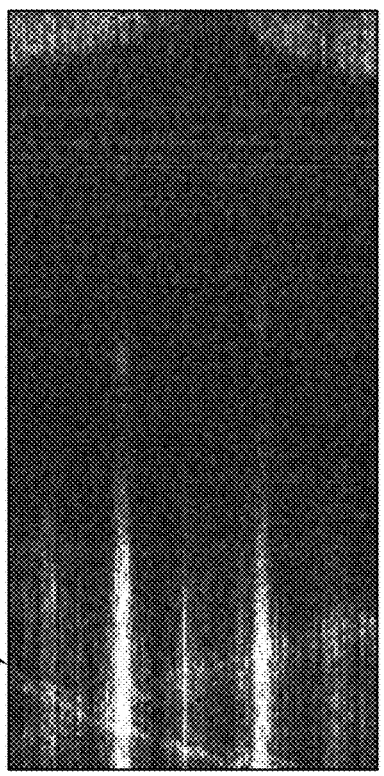

138

This is a cross correlation signal from the retina, during the signal search - this is an ghost/artifact that should be ignored - 140

FIG. 5e

Example of a cross correlation signal- Real signal, while reference mirror moving

| Time AU | Reference arm position AU |
|---|---|
| 4 | 60 |

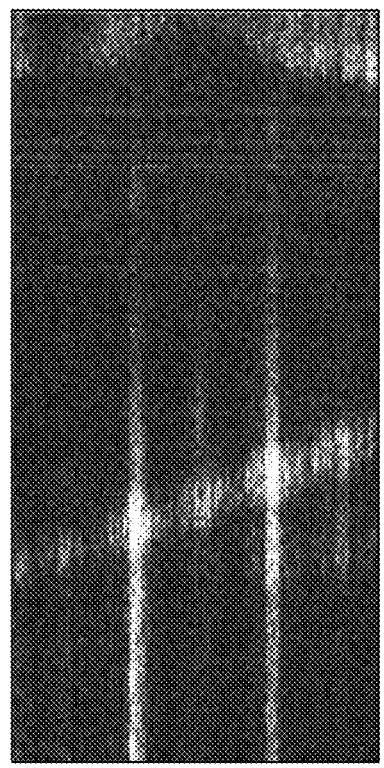

This is a cross correlation signal from the retina, during the signal search this is the "real" signal, the position of the reference mirror should be stored- 144

Example of a cross correlation signal- Real signal, while reference mirror moving

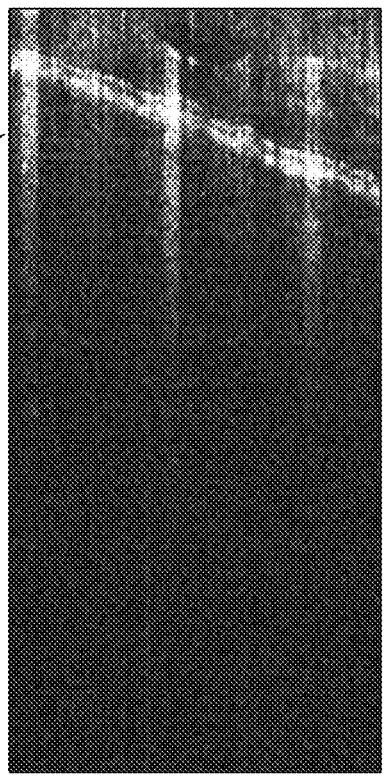

| Time AU | Reference arm position AU |
|---|---|
| 5 | 50 |

This is a cross correlation signal from the retina, during the signal search this is the "real" signal, the position of the reference mirror should be stored - 148

Example of a cross correlation signal- Real signal, while reference mirror moving This is a cross correlation signal from the retina, during the signal search this is the "real" signal, the position of the reference mirror should be stored- 152

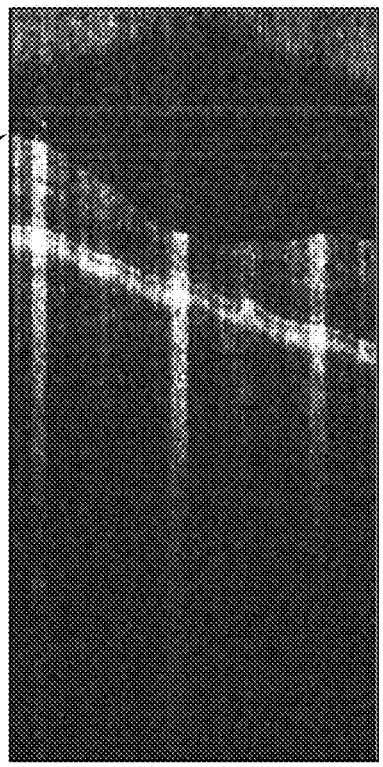

| Time AU | Reference arm position AU |
|---|---|
| 6 | 53 |

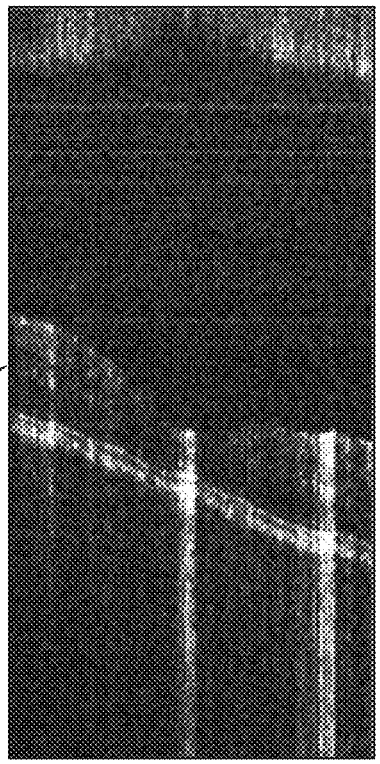

| Time AU | Reference arm position AU |
|---|---|
| X | X |

Example of a cross correlation signal- Real signal, while reference mirror moving This is a cross correlation signal from the retina, during the signal search - 156

154

Example of a cross correlation signal- Real signal, when reference mirror is static after focusing This is a cross correlation signal from the retina, during the signal search this is the "real" signal, while the reference mirror is static - 160

| Time AU | Reference arm position AU |
|---|---|
| 20 | 53 |

158

No "cross correlation" signal

— 162

Example of a cross correlation signal- Real signal, while reference mirror moving This is a cross correlation signal from the retina, during the signal search – this is the "real" signal, the position of the reference mirror should be stored - 166

— 164

Example of a cross correlation signal- Real signal, while reference mirror moving This is a cross correlation signal from the retina, during the signal search - this is the "real" signal, the position of the reference mirror should be stored - 170

168

Example of a cross correlation signal- Real signal, when reference mirror is static after focusing - 174

172

HOME OCT WITH AUTOMATIC FOCUS ADJUSTMENT

BACKGROUND

Macular degeneration is the leading cause of vision loss in the United States of America. In macular degeneration, the central portion of the retina (a.k.a., the macula) deteriorates. When healthy, the macula collects and sends highly detailed images to the brain via the optic nerve. In early stages, macular degeneration typically does not significantly affect vision. If macular degeneration progresses beyond the early stages, vision becomes wavy and/or blurred. If macular degeneration continues to progress to advanced stages, central vision may be lost.

Although macular degeneration is currently considered to be incurable, treatments do exist that may slow the progression of the disease so as to prevent severe loss of vision. Treatment options include injection of an anti-angiogenic drug into the eye, laser therapy to destroy an actively growing abnormal blood vessel(s), and photodynamic laser therapy, which employs a light-sensitive drug to damage an abnormal blood vessel(s). Early detection of macular degeneration is of paramount importance in preventing advanced progression of macular degeneration prior to treatment to inhibit progression of the disease. Timely treatment of advanced AMD is important to maintain the patient's vision.

Early detection of macular degeneration and timely treatment decisions can be accomplished using a suitable retinal imaging system. For example, Optical Coherence Tomography (OCT) is a non-invasive imaging technique relying on low coherence interferometry that can be used to generate a cross-sectional image of the macula. The cross-sectional view of the macula shows if the layers of the macula are distorted and can be used to monitor whether distortion of the layers of the macula has increased or decreased relative to an earlier cross-sectional image to assess the impact of treatment of the macular degeneration. Existing OCT imaging systems, however, are typically expensive and may have to be operated by a trained technician.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Optical coherence tomography (OCT) systems for imaging a user's retina, and related methods, employ a coupling optics assembly with no moving parts, a viewer assembly, a sample arm light beam focus mechanism, an OCT image detector, and a control unit. The viewer assembly is configured to restrains the user's head so as to maintain a fixed distance between the user's retina and the coupling optics assembly. The sample arm light beam focus mechanism is separate from the coupling optics assembly. The sample arm light beam focus mechanism provides focusing of the sample arm light beam onto the user's retina so as to account for the specific focusing characteristics of the user's eye. The control unit monitors an OCT signal generated by the OCT image detector while controlling variation of an operational parameter of the sample arm light beam focus mechanism over a range to identify a focus correction for the user, based on the OCT signal, for application to the sample arm light beam. Because the coupling optics assembly has no moving parts, the cost of the OCT system is reduced relative to OCT systems that employ coupling optics assemblies with moving parts. Additionally, since the OCT system is configured to image the retina while a fixed distance is maintained between the coupling optics assembly and the retina, the OCT system can be operated by the user without the assistance of a trained technician, thereby making the OCT system suitable for use in home-based imaging of the user's retina to monitor for the occurrence and/or progression of macular degeneration.

Thus, in one aspect, an optical coherence tomography (OCT) system for imaging a retina of a user is configured to be operated by the user and to have coupling optics with no moving parts. The OCT system includes a broad bandwidth light source, a beam splitter, a reference arm optical path, a reference arm optical path length adjustment mechanism, a sample arm optical path, an objective lens, a viewer assembly, a scanning unit, a sample arm light beam focus mechanism, an OCT image detector, and a control unit. The broad bandwidth light source emits a light beam. The beam splitter splits the light beam into a sample arm light beam and a reference arm light beam, and recombines the reference arm light beam with a returned portion of the sample arm light beam to form a recombined light beam. The reference arm light beam propagates over the reference arm optical path. The sample arm light beam and the returned portion of the sample arm light beam propagate over the sample arm optical path. The objective lens is disposed on the sample arm light path. The viewer assembly is configured to restrain the user's head so that the sample arm optical path extends to the retina. The scanning unit scans the sample arm light beam in two dimensions transverse to a direction of propagation of the sample arm light beam. The sample arm light beam focus mechanism is controllable to vary focus of the sample arm light beam on the retina. The OCT image detector generates an OCT signal for the recombined light beam. The control unit is operatively connected to the OCT image detector, the reference arm optical path length adjustment module, and the sample arm light beam focus mechanism. The control unit is configured to (a) monitor the OCT signal, (b) control the reference arm optical path length adjustment mechanism to vary the length of the reference arm optical path to identify a length of the reference arm optical path for which the OCT signal corresponds to an OCT image of the retina, and (c) vary an operational parameter of the sample arm light beam focus mechanism over a range, while maintaining the length of the reference arm optical path for which the OCT signal corresponds to the OCT image of the retina, to identify a focus correction for the user, based on the OCT signal, for application to the sample arm light beam.

In many embodiments, the OCT system includes a display device and a display device focus mechanism. A fixation target is displayed to the user via the display device. The display device focus mechanism is controllable to vary focus of an image of the fixation target on the retina. In many embodiments, the control unit is operatively connected to the display device focus mechanism. In many embodiments, the control unit is configured to: (a) determine a focus setting of the display device focus mechanism based on the identified focus correction for the user applied by the sample arm light beam focus mechanism, and (b) control the display device focus mechanism to operate at the focus setting of the display device focus mechanism. In some embodiments, the control unit uses a lookup data table to determine the focus setting of the display device focus mechanism corresponding to the identified focus correction for the user applied by the sample arm light beam focus mechanism. In some embodiments, the display device focus mechanism includes a display device focus lens that is repositionable relative to the display device, and the focus setting of the display device focus mechanism corresponds to a respective position of the display device focus lens relative to the display device. In some embodiments, the display device focus mechanism is operable to vary the focus of the image of the fixation target on the retina over at least a 15 diopter range. In some embodiments, the sample arm light beam focus mechanism is operable to vary the focus of the sample arm light beam on the retina over at least a 15 diopter range.

In many embodiments, the OCT system is configured to restrain the user's head to maintain the retina at a fixed position on the sample arm optical path. For example, in many embodiments, the viewer assembly is configured to engage facial features of the user to restrain the user's head and define a distance between the eye and the objective lens. The distance between the objective lens and the eye is not controlled by the OCT system or an operator of the OCT system.

Any suitable approach can be used to identify the length of the reference arm optical path for which the OCT signal corresponds to an OCT image of the retina. For example, the control unit can process the OCT signal to generate an OCT image that is processed by the control unit using an image processing approach to identify the length of the reference arm optical path for which the OCT signal corresponds to an OCT image of the retina.

Any suitable approach can be used to identify the focus correction for the user. For example, the control unit can process the OCT signal to generate an OCT image that is processed by the control unit using an image processing approach to identify focus correction for the user.

In many embodiments of the OCT system, the sample arm light beam focus mechanism is disposed on the sample arm optical path between the beam splitter and the scanning unit. In some embodiments, the sample arm light beam focus mechanism comprises a controllable liquid lens.

In some embodiments, the control unit: (a) controls the reference arm optical path length adjustment mechanism to vary the length of the reference arm optical path over a range that encompasses all lengths of the reference arm optical path length achievable via control of the reference arm optical path length adjustment mechanism, (b) determines candidate lengths for the reference arm optical path length, each of the candidate lengths being determined based on a respective strength of the OCT signal, and (c) selects one of the candidate lengths that has the highest respective strength of the OCT signal to be the length of the reference arm optical path for which the OCT signal corresponds to the OCT image of the retina. In some embodiments, the range that encompasses all lengths of the reference arm optical path length achievable via control of the reference arm optical path length adjustment mechanism covers no more than 50 mm.

In many embodiments, the OCT system is configured to monitor alignment of the user's pupil with the sample arm optical path. For example, in many embodiments, the OCT system includes a pupil camera, a pupil imaging optical path, a pupil illumination light source, and a dichroic mirror that couples the pupil imaging optical path with the sample arm optical path. In many embodiments, the control unit is operatively coupled with the pupil camera and processes output of the pupil camera to detect whether the pupil is open and aligned with the sample arm optical path. In many embodiments, the length of the reference arm optical path is varied only while the pupil is open and aligned with the sample arm optical path.

In many embodiments of the OCT system, the sample arm light beam focus mechanism is operable to vary the focus of the sample arm light beam on the retina over a suitable range to accommodate optical differences of a target population of users. For example, in some embodiments, the sample arm light beam focus mechanism is operable to vary the focus of the sample arm light beam on the retina over at least a 15 diopter range. In some embodiments, the sample arm light beam focus mechanism is operable to vary the focus of the sample arm light beam on the retina over no more than a 25 diopter maximum range In many embodiments, the OCT system is configured to produce an image of the retina that has a suitable level of resolution. For example, in some embodiments, the integration time for an a-scan is above 50 microseconds.

In many embodiments, the OCT system includes a telescope assembly that has no moving parts. For example, in many embodiments, the OCT system includes a telescope assembly that includes an objective lens and a second lens, wherein each of the objective lens and the second lens have a fixed position on the sample arm optical path.

In another aspect, a method of imaging a retina of a user with an OCT system is provided. The method includes emitting a light beam from a broadband light source. The light beam is split into a sample arm light beam and a reference arm light beam. The sample arm light beam propagates through a sample arm light beam focus mechanism to apply a focus correction to the sample arm light beam. The focus corrected sample arm light beam is scanned, by a scanning unit, in two dimensions transverse to a direction of propagation of the sample arm light beam to produce a scanned sample arm light beam. The scanned sample arm light beam is propagated through an objective lens. The user's head is restrained by a viewer assembly so that the scanned sample arm light beam is incident upon the retina. The reference arm light beam propagates over a reference arm light beam optical path. A returned portion of the scanned sample arm light beam is recombined with the reference arm light beam to produce a recombined light beam. The recombined light beam propagates to an OCT image detector. The OCT image detector generates an OCT signal for the recombined light beam. A control unit monitors the OCT signal. The control unit controls a reference arm optical path length adjustment mechanism to vary the length of the reference arm optical path to identify a length of the reference arm optical path for which the OCT signal corresponds to an OCT image of the retina. The control unit varies an operational parameter of the sample arm light beam focus mechanism over a range, while maintaining the length of the reference arm optical path for which the OCT signal corresponds to the OCT image of the retina, to identify a focus correction for the user, based on the OCT signal, for application to the sample arm light beam. In some embodiments, the sample arm light beam focus mechanism includes a controllable liquid lens.

In many embodiments, the method includes operating a display device focus mechanism at a setting corresponding to the identified focus correction for the user applied by the sample arm light beam focus mechanism. For example, in many embodiments, the method includes: (a) propagating light from a display device to the retina through a display device focus mechanism, (b) determining, by the control unit, a focus setting of the display device focus mechanism based on the identified focus correction for the user applied by the sample arm light beam focus mechanism, and (c) controlling the display device focus mechanism, by the control unit, to operate at the focus setting of the display device focus mechanism. In many embodiments of the method, the control unit accesses a lookup data table to determine the focus setting of the display device focus mechanism. In some embodiments of the method, the display device focus mechanism includes a display device focus lens that is repositionable relative to the display device, and the focus setting of the display device focus mechanism corresponds to a respective position of the display device focus lens relative to the display device. In some embodiments of the method, the display device focus mechanism is operable to vary the focus of the image of the fixation target on the retina over at least a 15 diopter range. In some embodiments of the method, the display device focus mechanism is operable to vary the focus of the image of the fixation target on the retina over no more than a 25 diopter maximum range. In some embodiments of the method, the sample arm light beam focus mechanism is operable to vary the focus of the sample arm light beam on the retina over at least a 15 diopter range. In some embodiments of the method, the sample arm light beam focus mechanism is operable to vary the focus of the sample arm light beam on the retina over no more than a 25 diopter maximum range.

In many embodiments of the method, the viewer assembly engages facial features of the user to restrain the user's head and define a distance between the eye and the objective lens. In many embodiments of the method, the distance between the objective lens and the eye is set by the facial features of the user and is not controlled by the OCT system or an operator of the OCT system.

In many embodiments of the method, the control unit: (a) controls the reference arm optical path length adjustment mechanism to vary the length of the reference arm optical path over a range that encompasses all lengths of the reference arm optical path length achievable via control of the reference arm optical path length adjustment mechanism, (b) determines candidate lengths for the reference arm optical path length, each of the candidate lengths being determined based on a respective strength of the OCT signal, and (c) selects one of the candidate lengths that has the highest respective strength of the OCT signal to be the length of the reference arm optical path for which the OCT signal corresponds to the OCT image of the retina. In some embodiments of the method, the range that encompasses all lengths of the reference arm optical path length achievable via control of the reference arm optical path length adjustment mechanism covers no more than 50 mm.

In many embodiments, the method includes processing output of a pupil camera, by the control unit, to detect whether the pupil is open and aligned with the sample arm optical path. In many embodiments of the method, the length of the reference arm optical path is varied only while the pupil is open and aligned with the sample arm optical path.

In many embodiments of the method, the sample arm light beam focus mechanism is operable to vary the focus of the sample arm light beam on the retina over a suitable range to accommodate optical differences of a target population of users. For example, in some embodiments, the sample arm light beam focus mechanism is operable to vary the focus of the sample arm light beam on the retina over at least a 15 diopter range.

In many embodiments of the method, an image of the retina is produced that has a suitable level of resolution. For example, in some embodiments of the method, the integration time for an a-scan is above 50 microseconds.

In many embodiments of the method, a telescope assembly that has no moving parts is employed. For example, in many embodiments of the method, the sample arm light beam propagates through a telescope assembly that includes an objective lens and a second lens, wherein each of the objective lens and the second lens have a fixed position on the sample arm optical path.

Any suitable approach can be used to identify the length of the reference arm optical path for which the OCT signal corresponds to an OCT image of the retina. For example, in some embodiments, the method includes processing the OCT signal, by the control unit, to generate an OCT image; and processing the OCT image, by the control unit, using an image processing approach to identify the length of the reference arm optical path for which the OCT signal corresponds to an OCT image of the retina.

Any suitable approach can be used to identify the focus correction for the user. For example, in some embodiments, the method includes processing the OCT signal, by the control unit, to generate an OCT image; and processing the OCT image, by the control unit, using an image processing approach to identify the focus correction for the user.

For a fuller understanding of the nature and advantages of the present invention, reference should be made to the ensuing detailed description and accompanying drawings.

BRIEF DESCRIPTION OF THE DRAWINGS

FIG. 5a through FIG. 5h show OCT images generated during a search for a reference arm path length for which the OCT signal corresponds to an OCT image of a strong eye retina.

DETAILED DESCRIPTION

Figure 1:
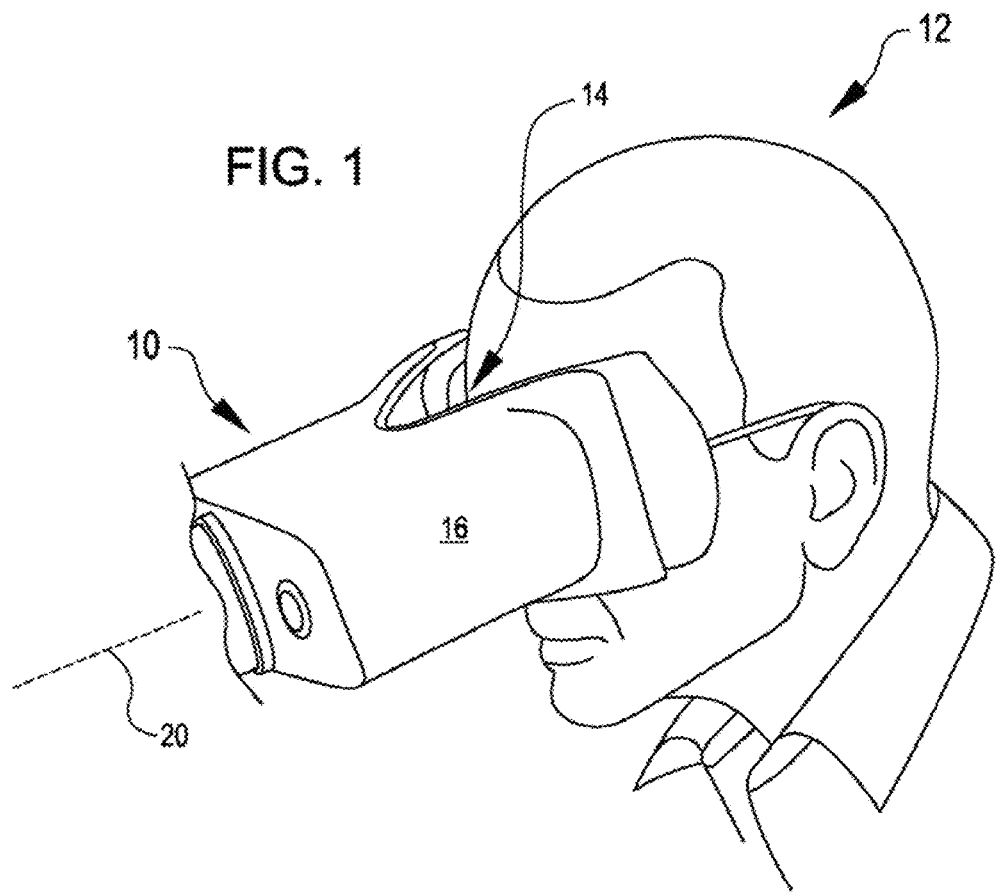
FIG. 1 shows a user looking into a view port of an optical coherence tomography (OCT) system for imaging a retina, in accordance with some embodiments.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Introduction

Many patients with retinal diseases are treated with intraocular injection per general guidelines based on the average patient. Progression of a retinal disease in any specific patient, may progress differently than in the average patient. Moreover, the specific patient may respond differently to treatment than the average patient. Accordingly, there is a strong clinical need to monitor the progression of a retinal disease in some patients on a continual basis so that the patient can receive treatment based on their own disease progression. Ophthalmic imaging devices employing optical coherence tomography (OCT) imaging are often employed in eye clinics to image a patient's retina to monitor the progression of a retinal disease. Having to travel to an eye clinic, however, may prevent sufficient continual monitoring of some patients. As a result, there is a need for affordable OCT based ophthalmic imaging devices that can be used by a patient at home to continually monitor the progression of the patient's retinal disease. Such retinal disease may be chorio-retinal eye diseases, such as AMD, ocular hystoplasmosis, myopia, central serous retinopathy, central serous choroidopathy, glaucoma, diabetic retinopathy, retintis pigmentosa, optic neuritis, epiretinal membrane, vascular abnormalities and/or occlusions, choroidal dystrophies, retinal dystrophies, macular hole, or choroidal or retinal degeneration.

OCT imaging of a retina often includes focusing a sample arm light beam onto the retina to enhance the resolution of the OCT image of the retina. Typically, OCT imaging of a retina is accomplished with the subject not wearing glasses or contacts. Variations between the optical characteristics of different eyes results in different amounts of focus correction being applied to the sample arm light beam for different subjects. Additionally, OCT imaging of a retina often includes the subject fixating on a fixation target so as to control eye orientation and accommodation level during an imaging session. The focus correction is typically applied so as to also focus the fixation target for the subject.

Many existing OCT systems apply a focus correction to the sample arm light beam using an approach that adds to the complexity of the system and/or requires a trained technician to operate the OCT system. For example, some existing OCT systems employ movement of an objective lens (i.e., a coupling optics lens located closest to the eye of the subject) relative to the eye to apply the focus correction. In some existing OCT systems, moving the objective lens relative to the eye is accomplished by a technician moving the OCT system relative to the eye. In some existing OCT systems, the OCT system moves the objective lens relative to the eye. Some existing OCT systems employ a focus detector, such as a fundus camera, that generates output indicative of how the sample arm light beam is currently focused on the retina for use in controlling the amount of focus correction applied to the sample arm light beam. Some existing OCT systems employ a coupling optics assembly, such as a telescope assembly, that includes two lenses, and varies the amount of focus correction applied to the sample arm light beam by varying the distance between the two lenses of the telescope assembly. A notable advantage of the approach used in many existing OCT systems to apply the focus correction to the sample arm light beam is that the same focus mechanism both focuses the sample arm light beam onto the retina and focuses the fixation target for the subject. In many existing systems, once the focus correction is applied, the length of the reference arm optical path is varied to search for the length of the reference arm optical path for which the OCT detector generates a signal from which an OCT image of the retina can be generated.

Added system complexity and/or the requirement for a trained technician to operate an OCT system, however, is undesirable in a home OCT system. For example, moving the objective lens relative to the retina may require movement of the OCT system relative to the retina, which complicates the operation of the OCT system. As another example, the use of a focus detector adds to the system complexity and cost.

Retinal Imaging OCT Systems for Use in a Non-Clinical Environment

Affordable retinal imaging OCT systems and related methods are described herein that are suitable for use in a non-clinical environment (e.g., at a patient's home), thereby serving to reduce the cost associated with monitoring of progression of a patient's retinal disease. Referring now to the drawings, in which like reference numerals represent like parts throughout the several views, FIG. 1 shows a user 12 looking into a view port 14 of a viewing assembly 16 of a retinal imaging OCT system 10, in accordance with many embodiments. In many embodiments, the viewing assembly 16 is configured to approximately position one eye of the user 12 on an optical axis 20 of the OCT system 10. For example, in the configuration shown in FIG. 1, the viewing assembly 16 is configured to approximately position the right eye of the user 12 on the optical axis 20. In many embodiments, the viewing assembly 16 is repositionable relative to the optical axis 20 so as to reconfigure the viewing assembly 16 to approximately position the left eye of the user 12 on the optical axis 20. Accordingly, each of the right eye and the left eye of the user 12 can be selectively approximately positioned on the optical axis 20 of the OCT system 10 for imaging of the respective eye by the retinal imaging OCT system 10. In embodiments described herein, final positioning and alignment of the optical axis of the respective eye of the user 12 with the optical axis 20 of the imaging system 10 is accomplished by the user 12 adjusting the user's position relative to the view port 14 in response to feedback provided to the user 12 by the OCT system 10.

Figure 2:
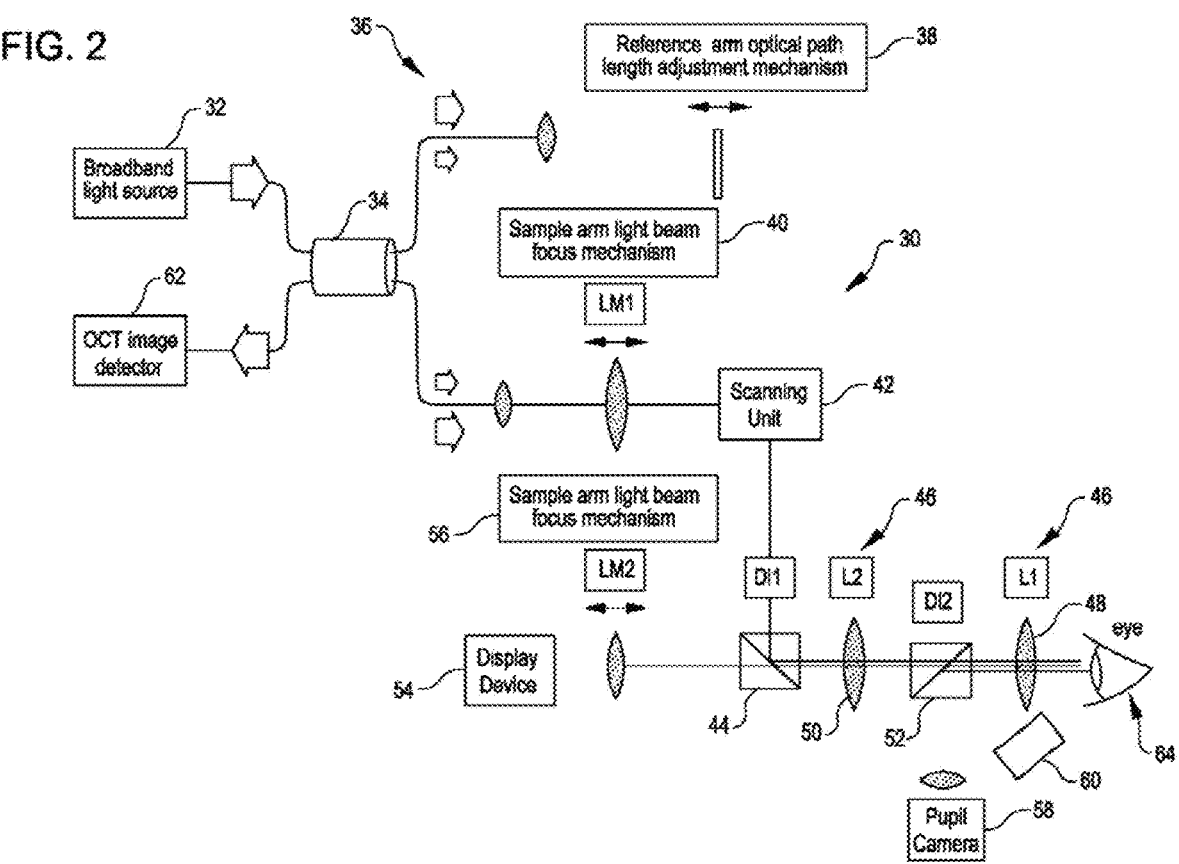
FIG. 2 is a simplified schematic illustration of components and associated optical paths of an OCT imaging device of the OCT system of FIG. 1.

FIG. 2 is a simplified schematic illustration of components and associated optical paths of an OCT imaging device 30 of the OCT system 10. The OCT imaging device 30 includes a broadband light source 32, a beam splitter 34, a reference arm optical path 36, a reference arm optical path length adjustment mechanism 38, a sample arm light beam focus mechanism 40, a scanning unit 42, a first dichroic mirror 44, a coupling optics assembly 46 that includes a fixed position objective lens 48 and a fixed position rear lens 50, a second dichroic mirror 52, a display device 54, a display device focus mechanism 56, a pupil camera 58, an eye illuminator 60, and an OCT image detector 62. In the illustrated embodiment, the OCT imaging device 30 is a spectral domain OCT imaging device that operates in a wavelength range of 800 nm to 900 nm. The eye illuminator 60 illuminates an eye 64 of the user 12 using a suitable wavelength of light (e.g., a wavelength of light above 920 nm). The display device 54 can project light between any suitable wavelength (e.g., from 400 nm to 700 nm). The first dichroic mirror 44 transmits the display device wavelength range and reflects the OCT wavelength. The second dichroic mirror 52 transmits the OCT wavelength and the display wavelength range (400 nm to 900 nm) and reflects the illumination wavelength (e.g., greater than 920 nm) to the pupil camera 58.

In operation, the broadband light source 32 emits a light beam having the OCT wavelength. The light beam propagates from the light source 32 to the beam splitter 34. The beam splitter splits the light beam into a sample arm light beam and a reference arm light beam.

The reference arm light beam propagates over a reference arm optical path 36 and then back to the beam splitter 34. The reference arm optical path 36 includes a reference arm optical path length adjustment module 38 that is operable, under the control of a control unit 64 (see FIG. 3), to selectively vary the length of the reference arm optical path 36. The reference arm optical path length adjustment module 38 can have any suitable configuration. For example, the reference arm optical path length adjustment module 38 can include a motorized movable mirror that is controllably displaceable.

The sample arm light beam propagates from the beam splitter 34 to the sample arm light beam focus mechanism 40. The sample arm light beam focus mechanism 40 is operable, under the control of the control unit 64, to selectively apply a focus correction to the sample arm light beam so as to focus the sample arm light beam onto the retina of the eye 64. The sample arm light beam focus mechanism 40 provides focusing of the sample arm light beam onto the user's retina so as to account for the specific focusing characteristics of the user's eye 64.

The sample arm light beam, with the applied focus correction, propagates from the sample arm light beam focus mechanism 40 to the scanning unit 42. The scanning unit 42 is operable, under the control of the control unit 64, to scan the sample arm light beam in two dimensions transverse to the direction of propagation of the sample arm light beam. The scanning unit 42 can have any suitable configuration. For example, in many embodiments, the scanning unit 42 includes dual axis scanning mirrors.

The scanned sample arm light beam propagates from the scanning unit 42 to the first dichroic mirror 44. The scanned sample arm light beam is reflected by the first dichroic mirror 44 so as to propagate through the coupling optics assembly 46 by propagating through the fixed position rear lens 50, the second dichroic mirror 52, and the fixed position objective lens 48. The scanned sample arm light beam propagates from the fixed position objective lens 48 into the eye 64 and onto the retina of the eye 64.

A returned portion of the scanned sample arm light beam propagates back from the retina and through the fixed objective lens 48, the second dichroic mirror 52, and the fixed rear lens 50. The returned portion of sample arm light beam is reflected by the first dichroic mirror 44 back to the scanning unit 42. The returned portion of the sample arm light beam is redirected by the scanning unit 42 back through the sample arm light beam focus mechanism 40 to the beam splitter 34. The returned portion of the sample arm light beam and the reference arm light beam are recombined by the beam splitter 34 to form a recombined light beam. The recombined light beam propagates to the OCT image detector 62.

The OCT image detector 62 generates and outputs an OCT image signal that is processed using known techniques to build up a three-dimensional OCT image of layers of the retina. In many embodiments, the OCT image detector 62 detects interference between the returning sample arm light and the reference arm light only if the time travelled by light in the reference and sample arms is nearly equal. In many embodiments, the reference arm optical path length adjustment module 38 includes a mirror that is mounted to a motorized mechanism that is controllable to vary the position of the mirror, thereby controllably varying the length of the reference arm optical path 36. The ability to vary the length of the reference arm optical path 36 enables the OCT imaging device 30 to be used to generate OCT images of any user's retina of a desired population of users even though each user's retina can be at a different distance from the fixed objective lens 48 when the user's head is engaged with the viewer assembly 16 due to corresponding anatomical variations between user's heads, as well as variation in the relative position between the user's head and the viewer assembly 16.

In many embodiments, the eye illuminator 60, the pupil camera 58, and the display device 54 are used to provide feedback to the user 12 by which the user 12 self-aligns the eye 64 with the optical axis of the OCT imaging device 30. The display device 54 displays a fixation target that is viewed by the user so as to align the eye 64 with the fixation target. The display device focus mechanism 56 is operable, under the control of the control unit 64, to selectively apply a focus correction light emitted by the display device 54 so that the fixation target displayed by the display device 54 is in focus for the user 12 even when the imaging of the user's retina is accomplished without the user 12 wearing glasses or contacts. Similar to the sample arm light beam focus mechanism 40, the display device focus mechanism 56 provides focusing of items displayed by the display device 54 (e.g., the fixation target) onto the user's retina so as to account for the specific focusing characteristics of the user's eye 64.

Figure 3:
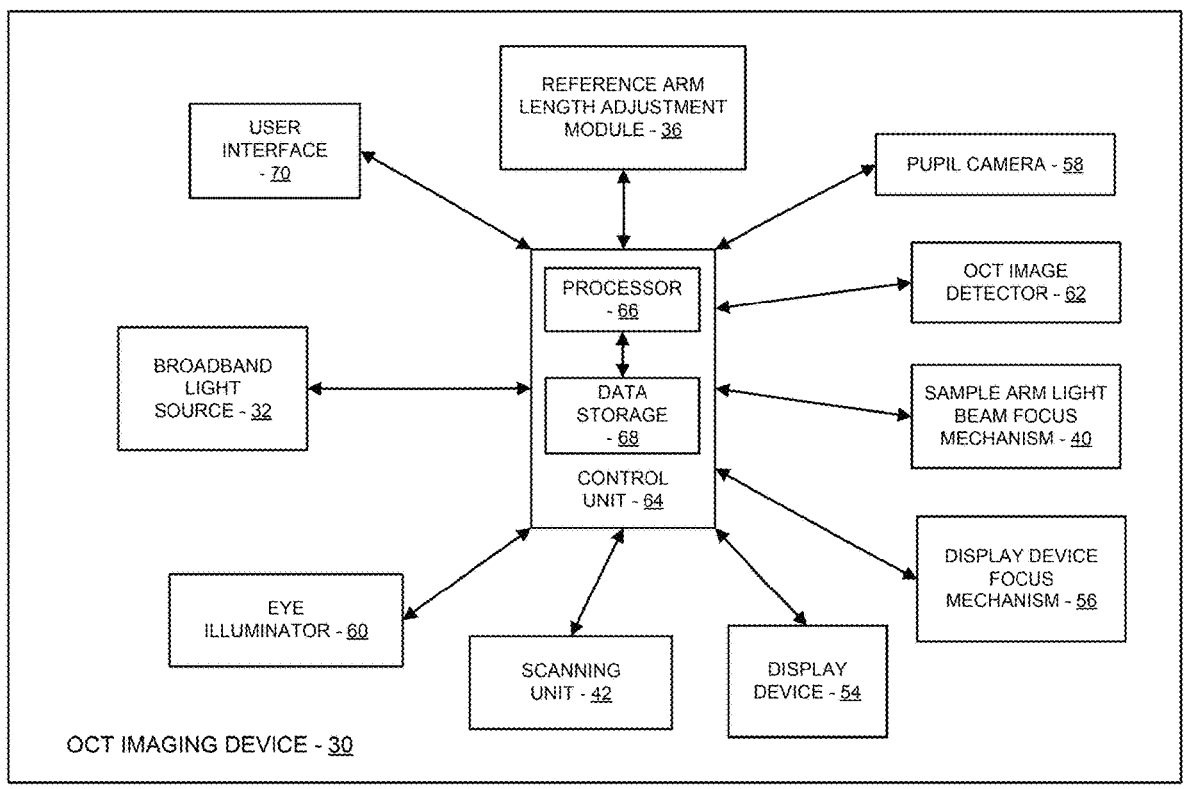
FIG. 3 is a simplified schematic diagram of components of the OCT system of FIG. 1.

In many embodiments, the OCT imaging device 30 is configured to automatically control components/modules of the OCT imaging device 30 during an imaging session during which an OCT image of a user's retina is generated. In many embodiments, the OCT imaging device 30 includes a suitable control unit that is operatively connected to components/modules of the OCT imaging device 30 and configured to communicate and/or control the components/modules. For example, FIG. 3 is a simplified schematic diagram illustrating components/modules of an embodiment of the OCT imaging device 30 that includes the control unit 64 operatively coupled with the components/modules. The control unit 64 includes a processor 66 and a data storage device 68. The data storage device 68 stores program instructions executable by the processor 66 to accomplish the acts described herein. The data storage device 68 can also stores user specific data that can be used by the processor 66 to customize its control of the operation of the OCT imaging device 30 to the specific user as described.

The control unit 64 is operatively connected to a user interface 70 to receive input from the user 12 via the user interface 70 and/or to display output to the user 12 via the user interface 70. Any suitable user interface 70 can be employed including, but not limited to, one or more push buttons, a display, a touch display, one or more indicator lights, and/or a speaker. The user interface 70 can be configured to enable a user to input an identification of the user for an imaging session so that the control unit 30 can employ parameters stored in the data storage device 68 when controlling the components/modules of the OCT imaging device 30 during an imaging session of a retina of the user 12.

The control unit 64 is operatively connected to the eye illuminator 60, the pupil camera 58, and the display device 54. The control unit 64 can turn the eye illuminator 60 on at the start of an imaging session and off at the end of an imaging session. In many embodiments, the control unit 64 turns the pupil camera 58 on at the start of the imaging session, receives image data from the pupil camera 58, processes the image data to track the position of the optical axis of the eye 64 relative to the optical axis of the OCT imaging device 30, and turns the pupil camera 58 off at the end of the imaging session. In many embodiments, the control unit 64 turns the display device 54 on at the start of the imaging session, generates and displays feedback to the user 12 on the display device 54 (e.g., the fixation target) to enable the user 12 to reposition the user's head relative to the viewer assembly 16 to sufficiently align the user's eye 64 with the optical axis of the OCT imaging device 30 for the generation of an OCT image of the user's retina, and turns the display device 54 of that the end of the imaging session.

The control unit 64 is operatively connected to the broadband light source 32, the reference arm optical path length adjustment module 38, the sample arm light beam focus mechanism 40, the scanning unit 42, the display device focus mechanism 56, and the OCT image detector 62 to control operation of and/or receive input from these components/modules during an OCT imaging session of a retina of the user 12. The control unit 64 can turn the broadband light source 32 on to begin transmission of the OCT wavelength light beam over the sample and reference arms at the beginning of the OCT scanning portion of the imaging session, and can turn the light source 32 off at the end of the imaging session. The control unit 64 can control the reference arm optical path length adjustment module 38 to vary the length of the reference arm optical path to search for the length of the reference arm optical path for which the OCT image detector 62 generates a suitable OCT signal for use in generating an OCT image of the user's retina. For example, the control unit 64 can receive and process the OCT signal generated by the OCT image detector 62 to monitor the suitability of the OCT signal to generate an OCT image of the user's retina while the control unit 64 controls the reference arm optical path length adjustment module 38 to vary the length of the reference arm optical path.

Following the identification of a suitable length of the reference arm optical path for use in generating an OCT image of the retina, the control unit 64 can control the sample arm light beam focus mechanism 40 to vary the amount of a focus correction applied to the sample arm light beam to search for a suitable focus correction for the user 12. In many embodiments, the control unit 64 monitors a strength of the OCT image signal generated by the OCT image detector 62 while varying the amount of focus correction applied to the sample beam to identify the focus correction that maximizes the monitored strength of the OCT image signal, thereby identifying a focus correction that results in the sample arm light beam being focused on the retina of the user 12. In some embodiments, an operational parameter of the sample arm light beam focus mechanism 40 is varied by the control unit 64, thereby resulting in a corresponding variation in the applied focus correction. In some embodiments, the data storage device 68 stores a data lookup table that provides correspondence between the varied operational parameter of the sample arm light beam focus mechanism and the diopter correction of the respective focus corrections. The sample arm light beam focus mechanism 40 can be operable to vary the amount of the applied focus correction over a suitable range to accommodate any user within a target population of users. For example, the sample arm light beam focus mechanism 40 can be configured to be operable to vary the amount of the applied focus correction over at least a 15 diopter range. The sample arm light beam focus mechanism 40 can have any suitable configuration. For example, in some embodiments, the sample arm light beam focus mechanism 40 includes a liquid lens that is controllable by the control unit 64 to vary the applied focus correction to identify the optimum focus correction for use during the OCT imaging session of the retina of the user 12. In some embodiments, the control unit 64 monitors output of the pupil camera 58 to monitor alignment of the user's pupil with the optical axis of the OCT imaging device 30. In some embodiments, the control unit 64 monitors output of the pupil camera 58 to monitor whether the user's eyelid is sufficiently open for the sample arm light beam to reach the retina. In some embodiments, the control unit 64 suspends the search for the focus correction to be applied by the sample arm light beam focus mechanism 40 while there is insufficient alignment of the user's eye with the optical axis of the OCT imaging device 30 or if the user's eyelid is not sufficiently open for the sample arm light beam to reach the retina.

Following the identification of a focus correction to be applied by the sample arm light beam focus mechanism 40 for the user 12, the control unit 64 can control operation of the display device focus mechanism 56 to apply a corresponding focus correction so that items displayed by the display device 54 (e.g., the fixation target) are in focus for the user 12. For example, if a 2.5 diopter focus correction is identified to be the focus correction to be applied by the sample arm light beam focus mechanism 40, the control unit 64 can control operation of the display device focus mechanism 56 to also apply a 2.5 diopter focus correction.

Figure 4A:
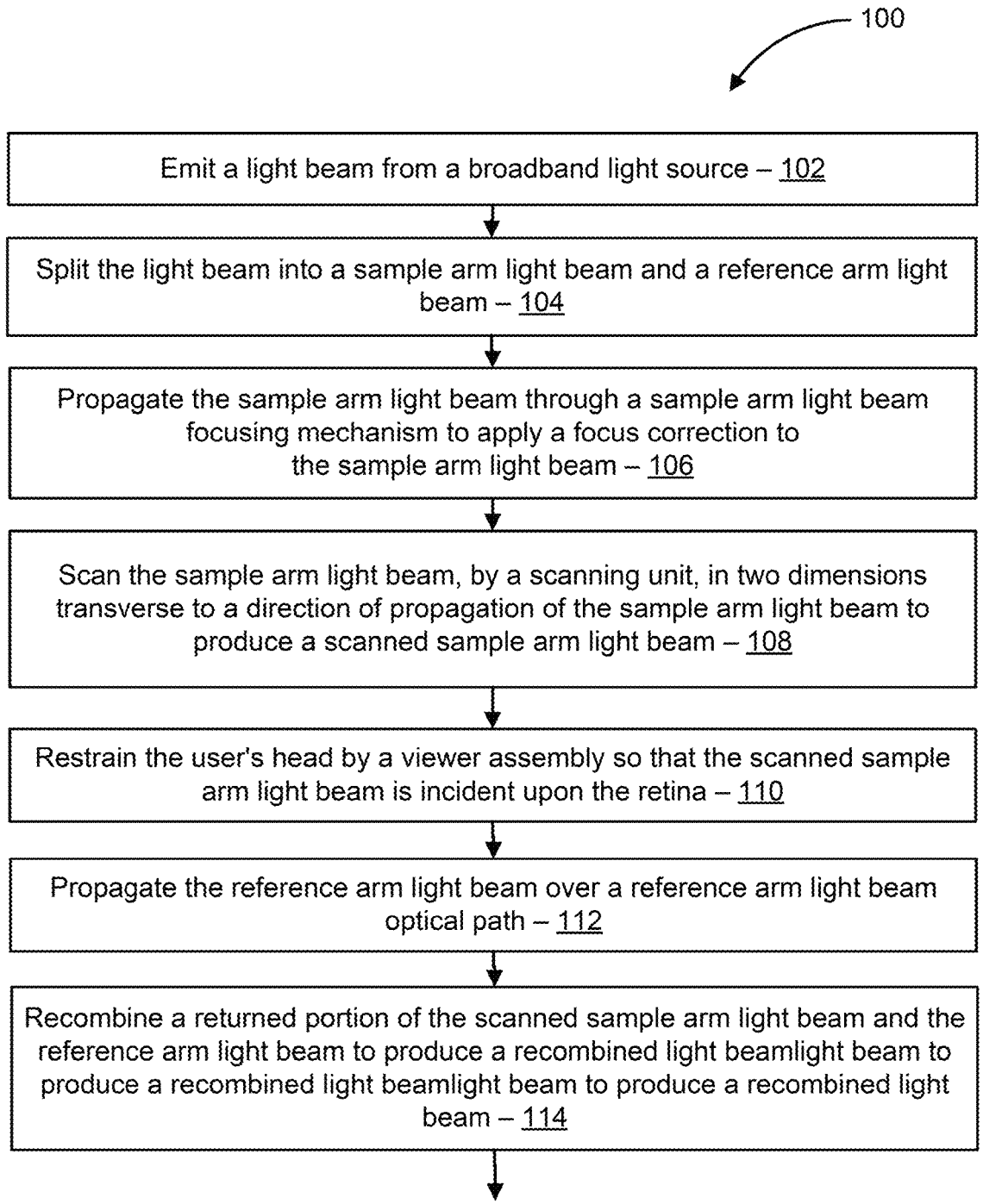
FIG. 4a and FIG. 4b show a simplified schematic block diagram of acts of a method of imaging a retina of a user, in accordance with embodiments.
Figure 4B:
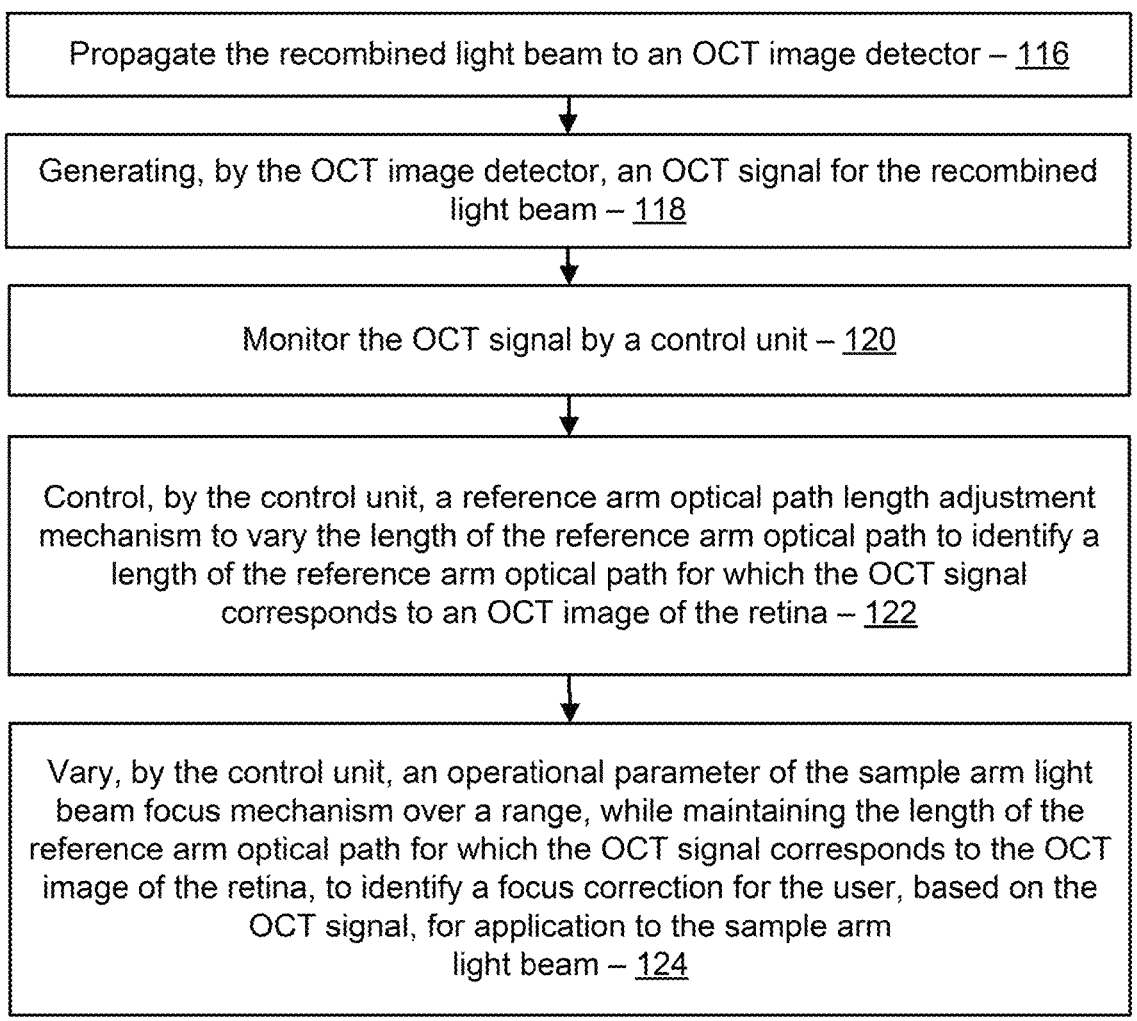

FIG. 4A and FIG. 4B show a simplified schematic block diagram of acts of a method 100 of imaging a retina by an OCT system, in accordance with embodiments. Any suitable OCT imaging system, such as the OCT system 10 described herein, can be used to practice the method 100.

In act 102, a light beam is emitted from a broadband light source. For example, in the OCT imaging device 30 of the OCT system 10, the control unit 64 can control operation of the broadband light source 32 to emit the light beam.

In act 104, the light beam is split into a sample arm light beam and a reference arm light beam. For example, in the OCT imaging device 30, the beam splitter 34 splits the light beam into the sample arm light beam and the reference arm light beam.

In act 106, the sample arm light beam propagates through a sample arm light beam focus mechanism to apply a focus correction to the sample arm light beam. For example, in the OCT imaging device 30, the sample arm light beam propagates through sample arm light beam focus mechanism 40, which applies the focus correction to the sample arm light beam.

In act 108, the sample arm light beam (with the focus correction applied) is scanned, by a scanning unit, in two dimensions transverse to a direction of propagation of the sample arm light beam to produce a scanned sample arm light beam. For example, in the OCT imaging device 30, the scanning unit 42 scans the sample arm light beam (with the focus correction applied by the sample arm light beam focus mechanism 40) in two dimensions transverse to a direction of propagation of the sample arm light beam.

In act 110, the user's head is restrained by a viewer assembly so that the scanned sample arm light beam is incident upon the retina. For example, in the OCT system 10, the user's head is restrained by the viewer assembly 16 assembly so that the scanned sample arm light beam is incident upon the retina. In many embodiments, the user's head is restrained by the viewer assembly 16 so that the eye 64 is maintained at a fixed distance from the fixed position objective lens 48.

In act 112, the reference arm light beam propagates over a reference arm light beam optical path. For example, in the OCT imaging device 30, the reference arm light beam propagates from the beam splitter 34 to the reference arm optical path length adjustment mechanism 38 and back to the beam splitter 34.

In act 114, a returned portion of the scanned sample arm light beam and the reference arm light beam are recombined to produce a recombined light beam. For example, in the OCT imaging device 30, the beam splitter 34 recombines a returned portion of the scanned sample arm light beam and the reference arm light beam to produce the recombined light beam.

In act 116, the recombined light beam propagates to an OCT image detector. For example, in the OCT imaging device 30, the recombined light beam propagates from the beam splitter 34 to the OCT image detector 62.

In act 118, the OCT image detector generates an OCT signal for the recombined light beam. For example, in the OCT imaging device 30, the OCT image detector 62 generates an OCT signal for the recombined light beam.

In act 120, the OCT signal is monitored by a control unit. For example, in the OCT imaging device 30, the control unit 64 monitors the OCT signal.

In act 122, a reference arm optical path length adjustment mechanism is controlled, by the control unit, to vary the length of the reference arm optical path to identify a length of the reference arm optical path for which the OCT signal corresponds to an OCT image of the retina. For example, in the OCT imaging device 30, the reference arm optical path length adjustment mechanism 38 is controlled, by the control unit 64, to vary the length of the reference arm optical path 36 to identify a length of the reference arm optical path 36 for which the OCT signal corresponds to an OCT image of the retina of the eye 64.

In act 124, an operational parameter of the sample arm light beam focus mechanism is varied, by the control unit, over a range, while maintaining the length of the reference arm optical path for which the OCT signal corresponds to the OCT image of the retina, to identify a focus correction for the user, based on the OCT signal, for application to the sample arm light beam. For example, in the OCT imaging device 30, an operational parameter of the sample arm light beam focus mechanism 38 is varied, by the control unit 64, over a range, while maintaining the length of the reference arm optical path 36 for which the OCT signal corresponds to the OCT image of the retina of the eye 64, to identify a focus correction for the user, based on the OCT signal, for application to the sample arm light beam.

FIG. 5*a* through FIG. 5*h* show a sequence of example OCT images generated during a search for a reference arm path length for which the OCT signal corresponds to an OCT image of a strong eye retina. The sequence of example OCT images shown illustrate aspects of the OCT images that can be identified using any suitable image processing approach to identify a reference arm path length for which the OCT signal corresponds to an OCT image of a strong eye retina.

FIG. 5*a* shows an example OCT image 126 at time (0) (arbitrary units (AU)) and the reference arm adjustable mirror position equal to 100 AU. The OCT image 126 includes an auto correlation signal 128 from the retina that can be ignored.

FIG. 5*b* shows an example OCT image 130 at time (1) AU and the reference arm adjustable mirror position equal to 90 AU. The OCT image 130 includes a cross correlation signal 132 from the retina. The cross correlation signal 132 is a ghost or an artifact that can be ignored.

FIG. 5*c* shows an example OCT image 134 at time (2) AU and the reference arm adjustable mirror position equal to 80 AU. The OCT image 134 includes a cross correlation signal 136 from the retina. The cross correlation signal 136 is a ghost or an artifact that can be ignored.

FIG. 5*d* shows an example OCT image 138 at time (3) AU and the reference arm adjustable mirror position equal to 70 AU. The OCT image 138 includes a cross correlation signal 140 from the retina. The cross correlation signal 140 is a ghost or an artifact that can be ignored.

FIG. 5*e* shows an example OCT image 142 at time (4) AU and the reference arm adjustable mirror position equal to 60 AU. The OCT image 142 includes a cross correlation signal 144 from the retina. The cross correlation signal 144 is a "real" signal from the retina and the corresponding reference arm optical path length and/or the position of the reference arm adjustable mirror position can be stored.

FIG. 5*f* shows an example OCT image 146 at time (5) AU and the reference arm adjustable mirror position equal to 50 AU. The OCT image 146 includes a cross correlation signal 148 from the retina. The cross correlation signal 148 is a "real" signal from the retina and the corresponding reference arm optical path length and/or the position of the reference arm adjustable mirror position can be stored.

FIG. 5*g* shows an example OCT image 150 at time (6) AU and the reference arm adjustable mirror position equal to 53 AU. The OCT image 150 includes a cross correlation signal 152 from the retina. The cross correlation signal 152 is a "real" signal from the retina and the corresponding reference arm optical path length and/or the position of the reference arm adjustable mirror position can be stored.

FIG. 5*h* shows an example OCT image 154 at time (7) AU and the reference arm adjustable mirror position equal to 58 AU. The OCT image 154 includes a cross correlation signal 156 from the retina. The cross correlation signal 156 is a "real" signal from the retina and the corresponding reference arm optical path length and/or the position of the reference arm adjustable mirror position can be stored.

Figure 6:
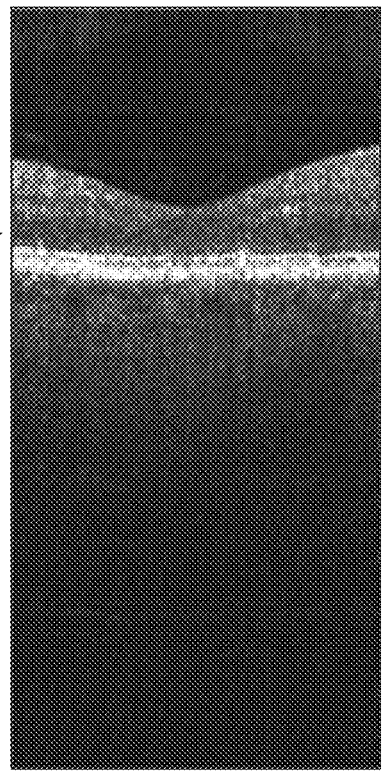
FIG. 6 shows an example OCT image for a reference arm path length for which the OCT signal corresponds to an OCT image of a strong eye retina after a user specific focus correction is applied to the sample arm light beam.

FIG. 6 shows an example OCT image 158 at a time (20) AU and the reference arm adjustable mirror position equal to 53 AU. The OCT image 158 was generated with a user specific focus correction applied to the sample arm light beam. The OCT image 158 includes a cross correlation signal 160 from the retina. The cross correlation signal 160 is a "real" signal from the retina. The reference arm adjustable mirror position and the user specific focus correction applied to the sample arm beam used to generate the OCT image 158 can be used to generate an OCT image of the strong eye retina.

Figure 7A:
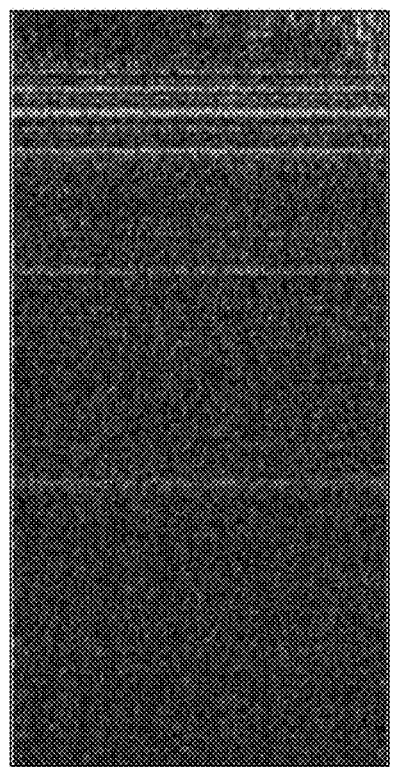
FIG. 7a through FIG. 7c show OCT images during a search for a reference arm path length for which the OCT signal corresponds to an OCT image of a weak eye retina.
Figure 7B:
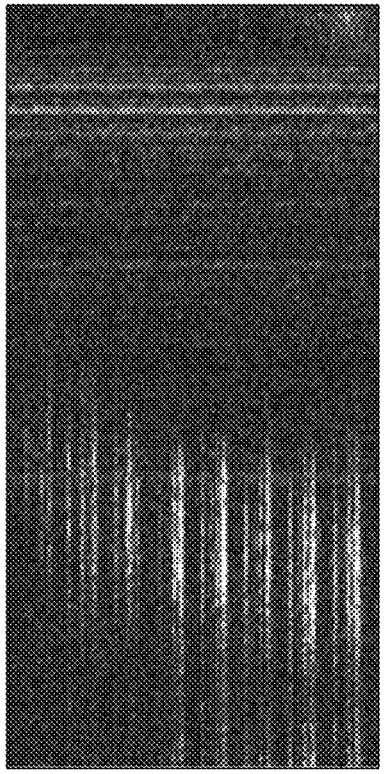
Figure 7C:
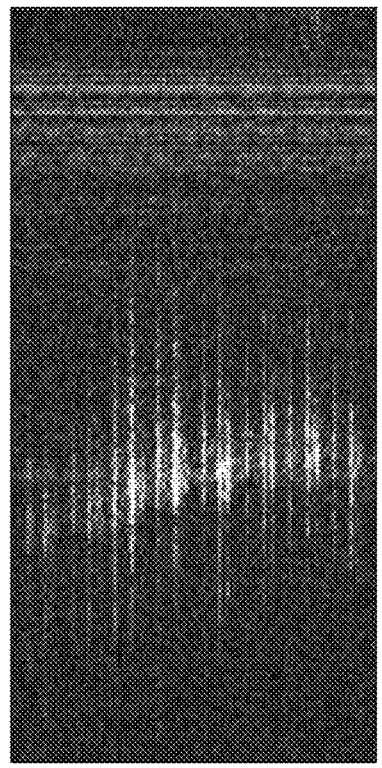

FIG. 7*a* through FIG. 7*c* show example OCT images generated during a search for a reference arm path length for which the OCT signal corresponds to an OCT image of a week eye retina. The sequence of example OCT images shown illustrate aspects of the OCT images that can be identified using any suitable image processing approach to identify a reference arm path length for which the OCT signal corresponds to an OCT image of a week eye retina. FIG. 7*a* shows an example OCT image 162 that does not include a cross correlation signal. FIG. 7*b* shows an example OCT image 164 that includes a cross correlation signal 166 from the retina. The cross correlation signal 166 is a "real" signal from the retina and the corresponding reference arm optical path length and/or the position of the reference arm adjustable mirror position can be stored. FIG. 7*c* shows an example OCT image 168 that includes a cross correlation signal 170 from the retina. The cross correlation signal 170 is a "real" signal from the retina and the corresponding reference arm optical path length and/or the position of the reference arm adjustable mirror position can be stored.

Figure 8:
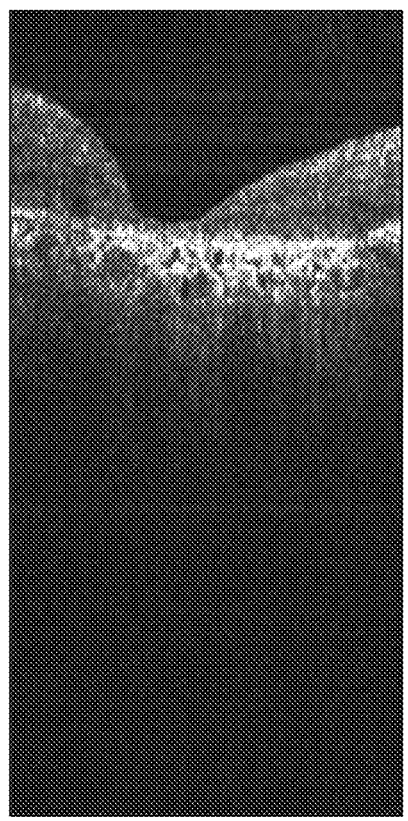
FIG. 8 shows an example OCT image for a reference arm path length for which the OCT signal corresponds to an OCT image of a weak eye retina after a user specific focus correction is applied to the sample arm light beam.

FIG. 8 shows an example OCT image 172 that was generated with a user specific focus correction applied to the sample arm light beam. The OCT image 172 includes a cross correlation signal 174 from the retina. The cross correlation signal 174 is a "real" signal from the retina. The reference arm adjustable mirror position and the user specific focus correction applied to the sample arm beam used to generate the OCT image 172 can be used to generate an OCT image of the strong eye retina.

Figure 9:
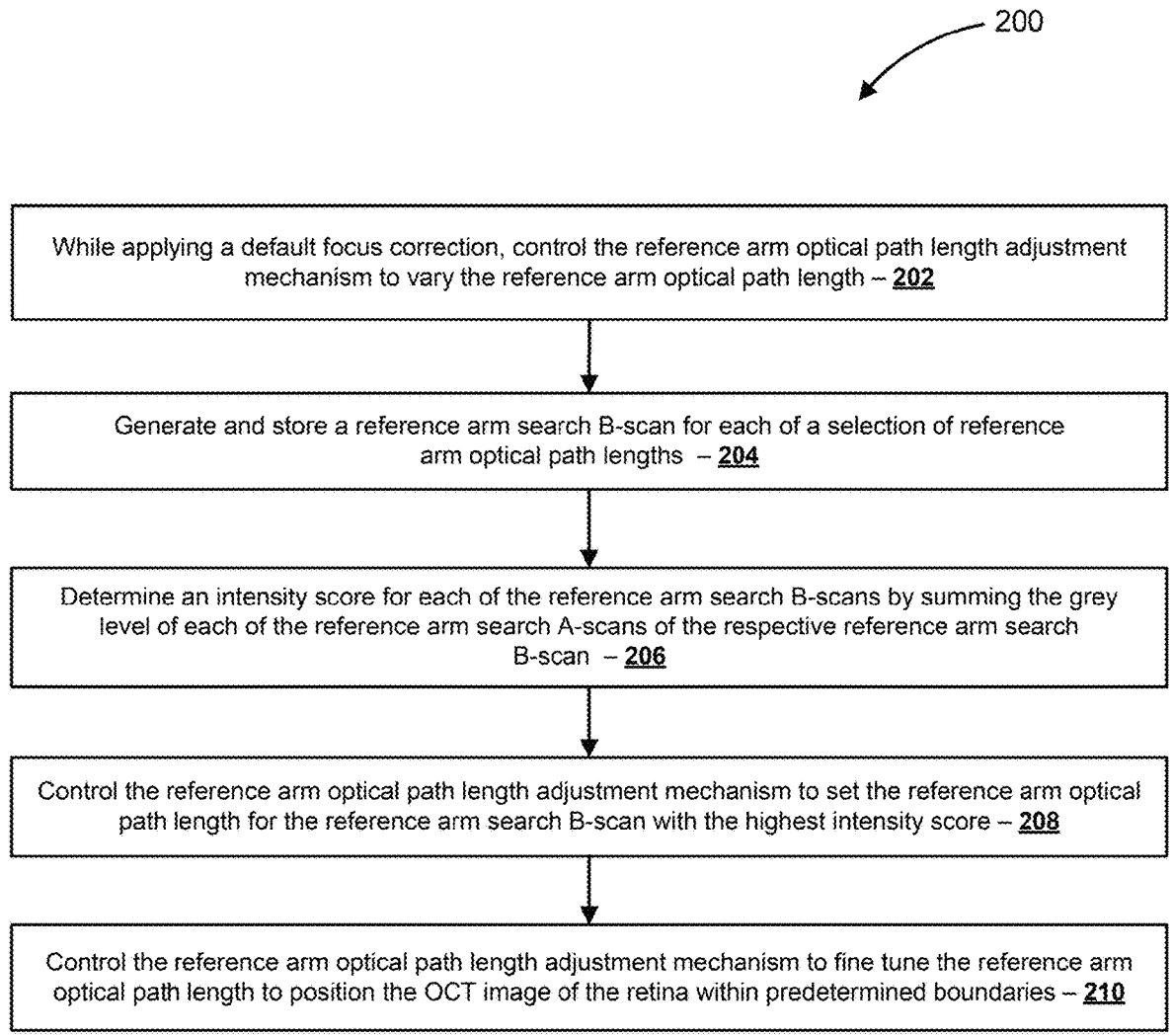
FIG. 9 shows a simplified schematic block diagram of acts of a process that can be used in the method shown in FIG. 4a and FIG. 4b to identify a reference arm optical path length for which the OCT signal corresponds to an OCT image of the retina.

FIG. 9 shows a simplified schematic block diagram of a process 200 that can be used to identify a reference arm optical path length for which the OCT image corresponds to an OCT image of the retina. The process 200 can be used to accomplish act 122 of the method 100.

In act 202, while applying a default focus correction (e.g., 0 diopter) to the sample arm light beam, the reference arm optical path length adjustment mechanism is controlled to vary the reference arm optical path length. For example, in the OCT imaging device 30, the control unit 64 controls the sample arm light beam focus mechanism 40 to apply the default focus correction to the sample arm path light beam. While the default focus correction is applied to the sample arm path light beam, the control unit 64 control the reference arm optical path length adjustment mechanism 38 to vary the length of the reference arm optical path 36.

In act 204, a reference arm search B-scan (a.k.a. cross-sectional tomography) is generated and stored for each of a selection of reference arm optical path lengths. The reference arm search B-scan can have any suitable number of reference arm search A-scans (a.k.a. axial depth scan). For example, in some embodiments, the reference arm search B-scan includes 500 reference arm search A-scans. In contrast, an imaging B-scan can be formed from the same number of A-scans as there are pixels in the OCT image detector, which can, for example, have 1024 pixels. For example, in the OCT imaging device 30, the control unit 64 processes an OCT signal generated by the OCT image detector 62 to generate a reference arm search B-scan for each of a selection of lengths of the reference arm optical path 36. The control unit 64 generates the reference arm search B scan by laterally combining a series of reference arm search A-scans. The control unit 64 controls the reference arm optical path length adjustment mechanism 38 to vary the reference arm optical path length around the respective selected reference arm optical path length so that the OCT image detector 62 generates an OCT signal that is processed by the control unit 64 to generate each of the reference arm search A-scans. Each reference arm search A-scan is indicative of the amount of the sample arm light beam that is reflected back from the location along the sample arm optical path corresponding to the respective reference arm optical path lengths. Accordingly, each reference arm search A-scan is indicative of a reflectively profile of the locations on the sample arm light beam corresponding to the reference arm search A-scan.

Figure 10:
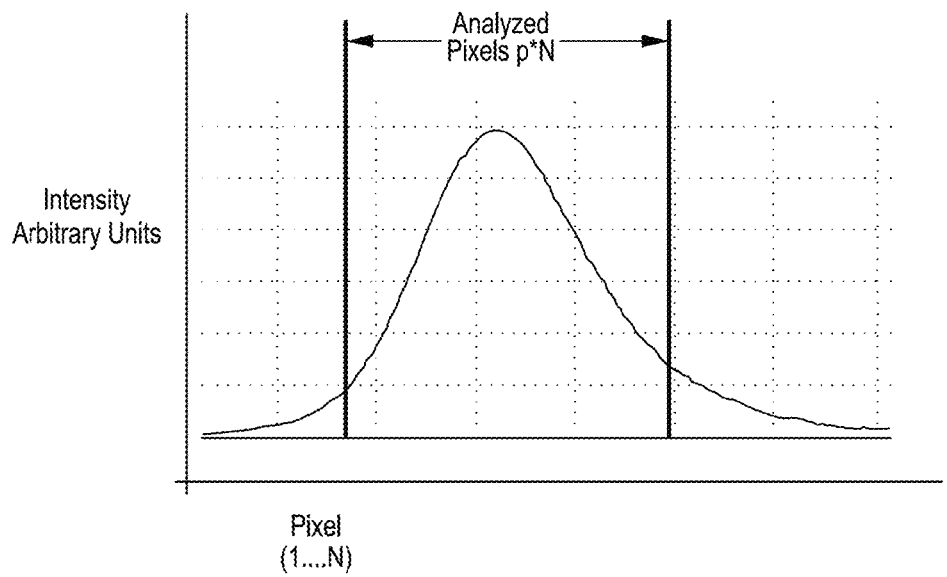
FIG. 10 shows an example spectrum on which a Fast Fourier Transformation is done to generate a respective A-scan in the process of FIG. 9.

Any suitable approach can be used to generate each of the reference arm search A-scans. For example, in the OCT imaging device 30, each spectrum output by the OCT image detector 62 can be processed by the control unit 64 using a Fast Fourier Transformation (FFT) to form a respective reference arm search A-scan. FIG. 10 shows an example spectrum on which a FFT is done to generate a respective reference arm search A-scan. In some embodiments, computational time is reduced during generation of the reference arm search A-scans by not including linearization and dispersion compensation.

In act 206, an intensity number is determined for each reference arm search B-scan by summing the gray level of each of the reference arm search A-scans in the respective reference arm search B-scan. For example, in the OCT imaging device 30, the control unit 64 determines an intensity number for each reference arm search B-scan by summing the gray level of each of the reference arm search A-scans in the respective reference arm search B-scan. In some embodiments, the intensity number has arbitrary units (AU).

In act 208, the reference arm optical path length is set to match the reference arm optical path length of the reference arm search B-scan with the highest intensity number. For example, in the OCT imaging device 30, the control unit 64 controls the reference arm optical path length adjustment mechanism 38 to set the reference arm optical path length to match the reference arm optical path length of the reference arm search B-scan with the highest intensity number.

Figure 11:
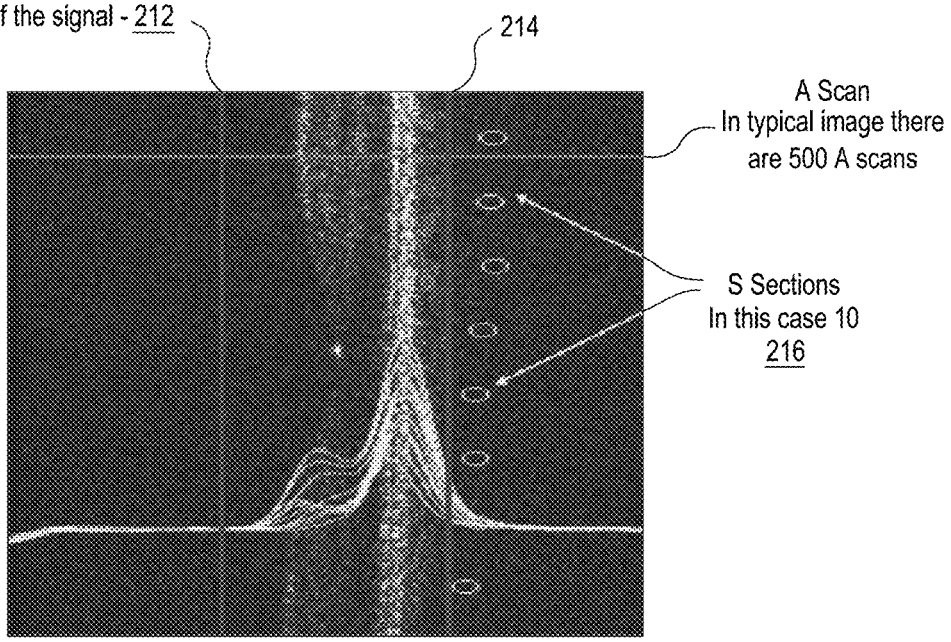
FIG. 11 shows an example OCT image during fine tuning of the reference arm optical path length in the process of FIG. 9.

In act 210, the reference arm optical path length is adjusted to fine tune the position of the image of the retina within predetermined boundaries. For example, in the OCT imaging device 30, the control unit 64 controls the reference arm optical path length adjustment mechanism 38 to fine tune the position of the image of the retina within predetermined boundaries. FIG. 11 shows an example OCT image during fine tuning of the reference arm optical path length to fine tune the position of the image of the retina within predetermined boundaries 212, 214. Any suitable approach can be used to detect the position of the image of the retina within the predetermined boundaries 212, 214. For example, a suitable image processing approach can be used that employs edge detection that is applied to a group of A scans to detect the position of the image of the retina relative to the predetermined boundaries 212, 214. The group of A-scans can include any suitable selection of A-scans. For example, in some embodiments, A-scans covering 10 different sections 216 are averaged to increase the reliability of edge detection based on the averaged A-scans. Any suitable number of A-scans can be included in each of the sections 216. For example, in some embodiments, 50 A-scans are included in each of the sections 216, and the 50 A-scans are averaged to detect an edged of the image of the retina. The sections 216 can be located relative to the predetermined boundaries 212, 214 so that when a corresponding edge of the image of the retina is disposed on the sections 216, the image of the retina is suitably located between the predetermined boundaries 212, 214. The direction of movement of the image of the retina for a change in the reference arm optical path length can be used to assess whether the image of the retina is a mirror image.

Figure 12:
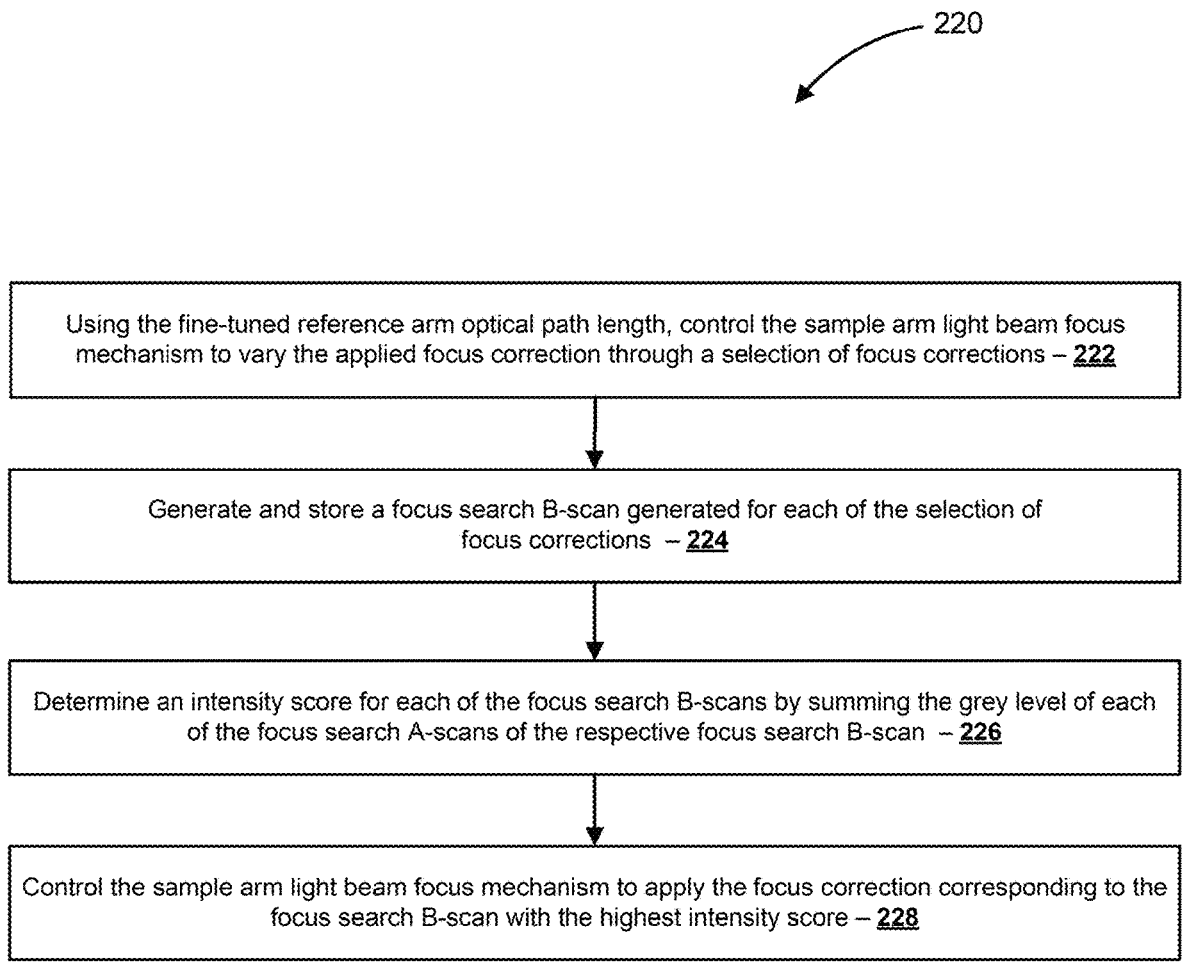
FIG. 12 shows a simplified schematic block diagram of acts of a process that can be used in the method shown in FIG. 4a and FIG. 4b to identify a user specific focus correction.

FIG. 12 shows a simplified schematic block diagram of acts of a process 220 that can be used in the method 100 to identify a user specific focus correction. The process 220 can be used to accomplish act 124 of the method 100.

In act 222, using the fine-tuned reference arm optical path length, the sample arm light beam focus mechanism is controlled to vary the applied focus correction through a selection of focus corrections. For example, in the OCT imaging device 30, the control unit 64 controls the sample arm light beam focus mechanism 40 to vary the focus correction applied to the sample arm light beam through a selection of focus corrections.

In act 224, a focus search B-scan is generated and stored for each of a selection of applied focus corrections. The focus search B-scan can have any suitable number of focus search A-scans (a.k.a. axial depth scan). For example, in some embodiments, the focus search B-scan includes 500 focus search A-scans. For example, in the OCT imaging device 30, the control unit 64 processes an OCT signal generated by the OCT image detector 62 to generate a focus search B-scan for each of a selection of lengths of the reference arm optical path 36. The control unit 64 generates the focus search B scan by laterally combining a series of focus search A-scans.

Any suitable approach can be used to generate each of the focus search A-scans. For example, in the OCT imaging device 30, each spectrum output by the OCT image detector 62 can be processed by the control unit 64 using a Fast Fourier Transformation (FFT) to form a respective focus search A-scan. In some embodiments, computational time for generating each focus search A-scan is reduced by not including linearization and dispersion compensation.

In act 226, an intensity score is determined for each focus search B-scan by summing the gray level of each of the focus search A-scans in the respective focus search B-scan. For example, in the OCT imaging device 30, the control unit 64 determines an intensity score for each focus search B-scan by summing the gray level of each of the focus search A-scans in the respective focus search B-scan. In some embodiments, the intensity score for each focus search B-scan has arbitrary units (AU).

In act 228, the sample arm light beam focus mechanism is controlled to apply the focus correction corresponding to the focus search B-scan with the highest intensity number. In some embodiments, interpolation using any suitable approach is employed to identify the best focus correction to apply when the amount of change in the intensity number between successive focus B-scans indicates that the best focus correction lies in between adjacent evaluated focus corrections.

Figure 13:
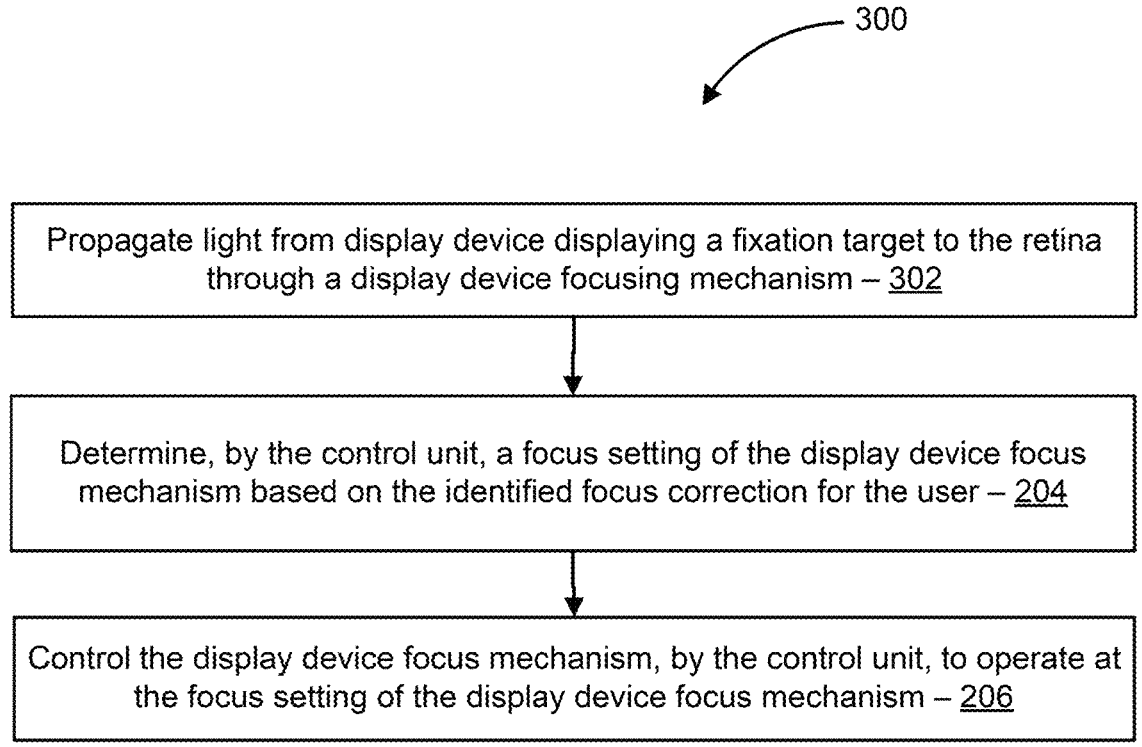
FIG. 13 shows a simplified schematic block diagram of acts of a process that can be accomplished in conjunction with the method shown in FIG. 4a and FIG. 4b.

FIG. 13 shows a simplified schematic block diagram of acts of a process 300 that can be accomplished in conjunction with the method 100. The process 300 can be used to operate a display device focus mechanism based on the identified focus correction for the user applied by the sample arm light beam focus mechanism that best focuses the sample arm light beam onto the retina.

In act 302, light is propagated from a display device to the retina through a display device focus mechanism. For example, in the OCT imaging device 30, light is propagated from the display device 54 through the display device focus mechanism 56.

In act 304, a focus setting of the display device focus mechanism is determined, by the control unit, based on the identified focus correction for the user applied via the sample arm light beam focus mechanism. For example, in the OCT imaging device 30, the control unit 64 determines a focus setting of the display device focus mechanism 56 based on the identified focus correction for the user applied via the sample arm light beam focus mechanism 40.

In act 306, the control unit controls the display device focus mechanism to operate at the focus setting for the display device focus mechanism. For example, in the OCT imaging device 30, the control unit 64 controls the display device focus mechanism 56 to operate at the focus setting for the display device focus mechanism 56.

Many of the features and approaches employed in the OCT imaging systems and related processes described herein provide benefits such as reduced cost and/or ease of operation. For example, the use of the sample arm light beam focus mechanism and acts described herein can be used in conjunction with a coupling optics assembly (e.g., a telescope) that has no moving parts. Additionally, the distance between the eye and the objective lens of the OCT imaging system can be fixed. For example, the distance between the eye and the objective lens can be defined by facial features (for example forehead—eye distance) engaged with a viewer assembly. Further, the use of the sample arm light beam focus mechanism and acts described herein can be used without the use of an additional detector that functions as a focus detector. The use of two separate focus mechanisms (i.e., a sample arm light beam focus mechanism and a display device focus mechanism) as described in conjunction with the OCT imaging systems and related processes described herein is believed to be counterintuitive in view of the use of a single focus mechanism (e.g., a coupling optics controllable to vary the focus) in many existing OCT imaging systems.

Many of the features and approaches employed in the OCT imaging systems and related processes described herein can be employed in combination with storage and reuse of user specific imaging parameters. For example, the reference arm optical path length and the applied focus correction identified and used during an initial imaging of a specific user's retina can be stored and used during subsequent imaging of the specific user's retina so as to reduce the range of the reference arm optical path lengths and the range of applied focus corrections searched during the subsequent imaging, thereby reducing the time required to conduct the subsequent imaging session. Any suitable approach can be used to store and reuse the user specific imaging parameters, such as the approaches described in U.S. patent application Ser. No. 16/424,246, entitled AUTOMATIC OPTICAL PATH ADJUSTMENT IN HOME OCT, filed May 28, 2019, the entire content of which is hereby incorporated herein by reference.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An optical coherence tomography (OCT) system for imaging a retina of an eye of a user, the OCT system comprising:
    a broad bandwidth light source that emits a light beam;
    a beam splitter that splits the light beam into a sample arm light beam and a reference arm light beam, and recombines the reference arm light beam with a returned portion of the sample arm light beam to form a recombined light beam;
    a reference arm optical path over which the reference arm light beam propagates;
    a reference arm optical path length adjustment mechanism operable to vary a length of the reference arm optical path;
    a sample arm optical path over which the sample arm light beam and the returned portion of the sample arm light beam propagate;
    an objective lens disposed on the sample arm optical path;
    a viewer assembly configured to restrain the user's head so that the sample arm optical path extends to the retina;
    a scanning unit that scans the sample arm light beam in two dimensions transverse to a direction of propagation of the sample arm light beam;
    a sample arm light beam focus mechanism controllable to vary focus of the sample arm light beam on the retina;
    an OCT image detector that generates an OCT signal for the recombined light beam;
    a display device that displays a fixation target viewable by the user via the retina; and
    a display device focus mechanism controllable to vary focus of an image of the fixation target on the retina, and
    a control unit operatively connected to the OCT image detector, the display device focus mechanism, the reference arm optical path length adjustment mechanism, and the sample arm light beam focus mechanism, the control unit being configured to:
    monitor the OCT signal;
        control the reference arm optical path length adjustment mechanism to vary the length of the reference arm optical path to identify a length of the reference arm optical path for which the OCT signal corresponds to an OCT image of the retina;
        vary an operational parameter of the sample arm light beam focus mechanism over a range, while maintaining the length of the reference arm optical path for which the OCT signal corresponds to the OCT image of the retina, to identify a focus correction for the user, based on the OCT signal, for application to the sample arm light beam;
        determine a focus setting of the display device focus mechanism based on the identified focus correction for the user applied by the sample arm light beam focus mechanism; and
        control the display device focus mechanism to operate at the focus setting of the display device focus mechanism.

2. The OCT system of claim 1, wherein the control unit uses a lookup data table to determine the focus setting of the display device focus mechanism corresponding to the identified focus correction for the user applied by the sample arm light beam focus mechanism.

3. The OCT system of claim 1, wherein:
    the display device focus mechanism comprises a display device focus lens that is repositionable relative to the display device; and
    the focus setting of the display device focus mechanism corresponds to a respective position of the display device focus lens relative to the display device.

4. The OCT system of claim 1, wherein the display device focus mechanism is operable to vary the focus of the image of the fixation target on the retina over at least a 15 diopter range.

5. The OCT system of claim 4, wherein the sample arm light beam focus mechanism is operable to vary the focus of the sample arm light beam on the retina over at least a 15 diopter range.

6. The OCT system of claim 1, wherein:
    the viewer assembly engages facial features of the user to restrain the user's head and define a distance between the eye and the objective lens; and
    the distance between the objective lens and the eye is not controlled by the OCT system or an operator of the OCT system.

7. The OCT system of claim 1, wherein the control unit processes the OCT signal to generate an OCT image that is processed using an image processing approach to accomplish at least one of:

the identification of the length of the reference arm optical path for which the OCT signal corresponds to an OCT image of the retina; and the identification of the focus correction for the user.

8. The OCT system of claim 1, wherein the sample arm light beam focus mechanism is disposed on the sample arm optical path between the beam splitter and the scanning unit.

9. The OCT system of claim 8, wherein the sample arm light beam focus mechanism comprises a controllable liquid lens.

10. The OCT system of claim 9, comprising:
a pupil camera;
a pupil imaging optical path;
a pupil illumination light source; and
a dichroic mirror to couple the pupil imaging optical path with the sample arm optical path, and wherein:
the control unit is operatively coupled with the pupil camera;
the control unit processes output of the pupil camera to detect whether the user's eye is open and aligned with the sample arm optical path; and
the length of the reference arm optical path is varied only while the user's eye is open and aligned with the sample arm optical path.

11. The OCT system of claim 1, wherein the control unit:
controls the reference arm optical path length adjustment mechanism to vary the length of the reference arm optical path over a range that encompasses all lengths of the reference arm optical path length achievable via control of the reference arm optical path length adjustment mechanism;
determines candidate lengths for the reference arm optical path length, each of the candidate lengths being determined based on a respective strength of the OCT signal; and
selects one of the candidate lengths that has the highest respective strength of the OCT signal to be the length of the reference arm optical path for which the OCT signal corresponds to the OCT image of the retina.

12. The OCT system of claim 11, wherein the range that encompasses all lengths of the reference arm optical path length achievable via control of the reference arm optical path length adjustment mechanism covers no more than 50 mm.

13. The OCT system of claim 11, comprising:
a pupil camera;
a pupil imaging optical path;
a pupil illumination light source; and
a dichroic mirror to couple the pupil imaging optical path with the sample arm optical path, and wherein:
the control unit is operatively coupled with the pupil camera;
the control unit processes output of the pupil camera to detect whether the user's eye is open and aligned with the sample arm optical path; and
the length of the reference arm optical path is varied only while the user's eye is open and aligned with the sample arm optical path.

14. The OCT system of claim 1, wherein the sample arm light beam focus mechanism is operable to vary the focus of the sample arm light beam on the retina over at least a 15 diopter range.

15. The OCT system of claim 1, wherein the integration time for an a-scan is above 50 microseconds.

16. The OCT system of claim 1, comprising a telescope assembly that includes an objective lens and a second lens, each of the objective lens and the second lens having a fixed position on the sample arm optical path.

17. An optical coherence tomography (OCT) system for imaging a retina of a user, the OCT system comprising:
a light source that emits a light beam;
a beam splitter that splits the light beam into a sample arm light beam and a reference arm light beam;
a reference arm optical path over which the reference arm light beam propagates;
a reference arm optical path length adjustment mechanism operable to vary a length of the reference arm optical path;
a scanning unit that scans the sample arm light beam in two dimensions transverse to a direction of propagation of the sample arm light beam;
a sample arm light beam focus mechanism controllable to vary focus of the sample arm light beam on the retina;
an OCT image detector that generates an OCT signal; and
a control unit operatively connected to the OCT image detector and the sample arm light beam focus mechanism, the control unit being configured to:
monitor the OCT signal;
vary an operational parameter of the sample arm light beam focus mechanism over a range to identify a focus correction for the user, based on the OCT signal, for application to the sample arm light beam;
control the reference arm optical path length adjustment mechanism to vary the length of the reference arm optical path over a range that encompasses all lengths of the reference arm optical path length achievable via control of the reference arm optical path length adjustment mechanism;
determine candidate lengths for the reference arm optical path length, each of the candidate lengths being determined based on a respective strength of the OCT signal; and
select one of the candidate lengths that has the highest respective strength of the OCT signal to be the length of the reference arm optical path for which the OCT signal corresponds to the OCT image of the retina.

18. The OCT system of claim 17, wherein the sample arm light beam focus mechanism is disposed between the beam splitter and the scanning unit.

19. The OCT system of claim 18, wherein the sample arm light beam focus mechanism comprises a controllable liquid lens.

20. The OCT system of claim 17, wherein the sample arm light beam focus mechanism comprises a controllable liquid lens.

21. The OCT system of claim 17, wherein the sample arm light beam focus mechanism is operable to vary the focus of the sample arm light beam on the retina over at least a 15 diopter range.

* * * * *